(12) United States Patent
Clark et al.

(10) Patent No.: US 7,357,931 B2
(45) Date of Patent: *Apr. 15, 2008

(54) USE OF SERUM AMYLOID A GENE IN DIAGNOSIS AND TREATMENT OF GLAUCOMA AND IDENTIFICATION OF ANTI-GLAUCOMA AGENTS

(75) Inventors: Abbot F. Clark, Arlington, TX (US); Wan-Heng Wang, Grapevine, TX (US); Loretta McNatt, Hurst, TX (US)

(73) Assignee: Alcon, Inc., Hunenberg (CH)

( * ) Notice: Subject to any disclaimer, the term of this patent is extended or adjusted under 35 U.S.C. 154(b) by 140 days.

This patent is subject to a terminal disclaimer.

(21) Appl. No.: 11/000,757

(22) Filed: Dec. 1, 2004

(65) Prior Publication Data

US 2005/0153927 A1    Jul. 14, 2005

Related U.S. Application Data

(60) Provisional application No. 60/530,430, filed on Dec. 17, 2003.

(51) Int. Cl.
*A61K 39/00* (2006.01)
(52) U.S. Cl. ..................................... 424/184.1; 514/2
(58) Field of Classification Search ............... None
See application file for complete search history.

(56) References Cited

U.S. PATENT DOCUMENTS

| 4,656,127 | A | 4/1987 | Mundy |
| 4,998,617 | A | 3/1991 | Ladd, Jr. et al. |
| 5,459,039 | A | 10/1995 | Modrich et al. |
| 5,545,628 | A | 8/1996 | Deboeck et al. |
| 5,593,826 | A | 1/1997 | Fung et al. |
| 6,433,018 | B1 | 8/2002 | Siddiqui et al. |
| 2002/0102581 | A1 | 8/2002 | Hageman et al. |

FOREIGN PATENT DOCUMENTS

| FR | 2650840 A1 | 8/1989 |
| WO | WO 91/02087 A1 | 2/1991 |
| WO | WO 92/15712 A1 | 9/1992 |
| WO | WO 94/16101 A3 | 7/1994 |

OTHER PUBLICATIONS

Barany, Proc. Natl. Acad. Sci. USA 88:189-193 (1991).
Bengtsson, Br. J Ophthalmol, vol. 73, pp. 483-487 (1989).
Cohen, et al., Adv. Chromatog. 36:127-162 (1996).
Cotton, et al., Proc. Natl. Acad. Sci. USA 85:4397-4401 (1988).
Cotton, Mutat. Res. 285:125-144 (1993).
Cronin, et al., Human Mutation, 7:244-255 (1996).
Ermilov et al., Arkh Patol., Abstract (1993).
Furlenato CJ et al., Biochem. Biophys.. Res. Commun. 268:405-408 (2002).
Gasparini, et al., Mol. Cell Probes 6:1-7 (1992).
Gibbs, et al., Nucleic Acids Res. 17:2437-2448 (1989).
Griffin, et al., Appl. Biochem Biotechnol. 38:147-159 (1993).
Guatelli, J. C., et al., Proc. Natl. Acad. Sci. USA 87:1874-1878 (1990).
Hayashi, Genet. Anal. Tech. Appl. 9(3):73-79 (1992).
He et al., Blood 101:1572-1581 (2003).
Hsu, et al., Carcinogenesis 15:1657-1662 (1994).
Jardat MS, et al., Planta Med. 68:667-71 (2002).
Jensen LE and Whitehead AS, Biochem. J. 334:489-503 (1998).
Kane et al., J. Neurochem., 72: 1939-1947 (1999).
Keen, et al., Trends Genet. 7:5 (1991).
Kornher, J. S., et al., Nucl. Acids Res. 17:7779-7784 (1989).
Krasnov et al., Vestn Oftalmol., Abstract, (1996).
Kumon et al., Amyloid 9:237-241 (2002a).
Kumon et al., Scand. J. Immunol. 56:504-511 (2002b).
Kumon et al., Scand J. Immunol. 53:7-12 (2001).
Kuppuswamy, M. N., et al., Proc. Natl. Acad. Sci. USA 88:1143-1147 (1991).
Kwoh, D. Y., et al., Proc. Natl. Acad. Sci. USA 86:1173-1177 (1989).
Lambert et al., Proc. Nat. Acad. Sci. USA 95: 6448-6453 (1998).
Landegren, U., et al., Science 241:1077-1080 (1988).
Leske MC, et al., American Journal of Epidemiology 118(2):166-191 (Aug. 1983).
Liang JS et al., Neurosci. Lett. 225:73-76 (1997).
Liu, et al., ARVO Abstract No. 1028 (2002).
Lizardi, P. M., et al., Bio/Technology 6:1197-1202 (1988).
Maxam and Gilbert, Proc. Natl. Acad. Sci. USA 74:560-564 (1977).
Milda T et al., Biochem. 38(51):16958-16962 (1999).
Miller, Genome Biology 3(1):reviews 3001.1-3001.15 (2001).
Myers, et al., Nature 313:495-498 (1985a).
Myers, et al., Science 230:1242-1246 (1985b).
Nakagami et al., Eur. J. Pharmacol. 457: 11-17 (2002a).
Nakagami et al., Br. J. Pharmacol., 137:676-682 (2002b).
Nickerson, D. A., et al., Proc. Natl. Acad. Sci. USA 87:8923-8927 (1990).
Nyren, P., et al., Anal. Biochem. 208:171-175 (1993).
O'Hara et al., Arthritis Res. 2:142-144 (2000).
Orita, et al., Proc. Natl. Acad. Sci. USA 86:2766-2770 (1989).
Pike et al., J. Neurosci. 13: 1676-1687 (1993).
Prezant, T. R., et al., Hum. Mutat. 1:159-164 (1992).
Prossner, Tibtech 11:238-246 (1993).
Roest, et al., Hum. Mol. Genet. 2:1717-1721 (1993).
Rosenbaum and Reissner, Biophys. Chem. 265:12753 (1987).
Saiki, et al., Nature 324:163-166 (1986).
Saiki, et al., Proc. Natl. Acad. Sci. USA 86:6230-6234 (1989).
Saleeba, et al., Methods in Enzymol. 217:286-295 (1992).
Sanger, et al., Proc. Natl. Acad. Sci. USA 74:5463-5467 (1977).
Schwartz et al., American Academy of Ophthalmology 89(4):394-401 (1982).
Sokolov, B.P., Nucl. Acids Res. 18:3671 (1990).
Strong, N. P., Ophthal. Physiol. Opt. 12:3-7 (1992).

(Continued)

Primary Examiner—Robert Mondesi
Assistant Examiner—Anand Desai
(74) Attorney, Agent, or Firm—Teresa J. Schultz

(57) ABSTRACT

The present invention provides compositions and methods for treating glaucoma, methods for diagnosing glaucoma, and methods for identifying agents which may be useful in the treatment of glaucoma. More specifically, the present invention describes the use of agents that modulate the expression of serum amyloid A.

1 Claim, 6 Drawing Sheets

OTHER PUBLICATIONS

Syvanen, A-C., et al., Genomics 8:684-692 (1990).
Thorn, CF, et al., J. Immunol. 169:399-406 (2002).
Tobe, et al., Nucleic Acids Res. 24:3728-3732 (1996).
Ugozzoli, L., et al., Gata 9:107-112 (1992).
Uhlar, CM and Whitehead, AS, Eur. J. Biochem. 265:501-523 (1999).
Urieli-Shoval et al., Journal of Histochemistry & Cytochemistry, 467(12):1377-1384 (1998).
van der Luijt, et al., Genomics 20:1-4 (1994).
Vaughan, D., et al., In: General Ophthalmology, Appleton & Lange, Norwalk, Conn., pp. 213-230 (1992).
Yamazaki et al., Biochemical And Biophysical Res. Comm., 290:1114-1122 (2002).
Yankner et al., Science 250: 279-282 (1990).
Zhang et al., Neurosci. Lett.. 312: 125-128 (2001).

Hagihara K et al, 2004, "IL-6 plays a critical role in the synergistic induction of human serum Amyloid A (SAA) gene when stimulated with proinflammatory cytokines as analysed with an SAA . . . ", Biochemical and Biophysical Research Communications, 314, 363-369, especially Abstract, and Figure 4 describing AG490.

International Search Report of a related PCT Application No. PCT/US04/40156, mailed Jul. 26, 2006.

Uhlar C et al., 1997, "Use of the acute phase serum anyloid A2 (SAA2) gene promoter in the analysis of pro- and anti-inflammatory mediators: differential kinetics of SAA2 promoter induction by IL-1 beta and TNF-alpha compared to IL06", Journal of Immunological Methods, 203, 123-130, especially Abstract.

Written Opinion of the International Searching Authority of a related PCT Application No. PCT/US04/40156, mailed Jul. 26, 2006.

USE OF SERUM AMYLOID A GENE IN DIAGNOSIS AND TREATMENT OF GLAUCOMA AND IDENTIFICATION OF ANTI-GLAUCOMA AGENTS

This application claims priority from the provisional application, U.S. Pat. Application Ser. No. 60/530,430 filed Dec. 17, 2003.

BACKGROUND OF THE INVENTION

1. Field of the Invention

The present invention relates to the field of diagnosis and treatment of glaucoma. More specifically, the invention provides methods and compositions for diagnosing and treating glaucoma and for identifying agents potentially useful for the treatment of glaucoma.

2. Description of the Related Art

There are a number of ocular conditions that are caused by, or aggravated by, damage to the optic nerve head, degeneration of ocular tissues, and/or elevated intraocular pressure. For example, "glaucomas" are a group of debilitating eye diseases that are a leading cause of irreversible blindness in the United States and other developed nations. Primary Open Angle Glaucoma ("POAG") is the most common form of glaucoma. The disease is characterized by the degeneration of the trabecular meshwork, leading to obstruction of the normal ability of aqueous humor to leave the eye without closure of the space (e.g., the "angle") between the iris and cornea (Vaughan, D. et al., (1992)). A characteristic of such obstruction in this disease is an increased intraocular pressure ("IOP"), resulting in progressive visual loss and blindness if not treated appropriately and in a timely fashion. The disease is estimated to affect between 0.4% and 3.3% of all adults over 40 years old (Leske, M. C. et al. (1986); Bengtsson, B. (1989); Strong, N. P. (1992)). Moreover, the prevalence of the disease rises with age to over 6% of those 75 years or older (Strong, N. P., (1992)).

Glaucoma affects three separate tissues in the eye. The elevated IOP associated with POAG is due to morphological and biochemical changes in the trabecular meshwork (TM), a tissue located at the angle between the cornea and iris. Most of the nutritive aqueous humor exits the anterior segment of the eye through the TM. The progressive loss of TM cells and the build-up of extracellular debris in the TM of glaucomatous eyes leads to increased resistance to aqueous outflow, thereby raising IOP. Elevated IOP, as well as other factors such as ischemia, cause degenerative changes in the optic nerve head (ONH) leading to progressive "cupping" of the ONH and loss of retinal ganglion cells and axons. The detailed molecular mechanisms responsible for glaucomatous damage to the TM, ONH, and the retinal ganglion cells are unknown.

Twenty years ago, the interplay of ocular hypertension, ischemia and mechanical distortion of the optic nerve head were heavily debated as the major factors causing progression of visual field loss in glaucoma. Since then, other factors including excitotoxicity, nitric oxide, absence of vital neurotrophic factors, abnormal glial/neuronal interplay and genetics have been implicated in the degenerative disease process. The consideration of molecular genetics deserves some discussion insofar as it may ultimately define the mechanism of cell death, and provide for discrimination of the various forms of glaucoma. Within the past 10 years, over 15 different glaucoma genes have been mapped and 7 glaucoma genes identified. This includes six mapped genes (GLC1A-GLC1F) and two identified genes (MYOC and OPYN) for primary open angle glaucoma, two mapped genes (GLC3A-GLC3B) and one identified gene for congenital glaucoma (CYP1B1), two mapped genes for pigmentary dispersion/pigmentary glaucoma, and a number of genes for developmental or syndromic forms of glaucoma (FOXC1, PITX2, LMX1B, PAX6).

Thus, each form of glaucoma may have a unique pathology and accordingly a different therapeutic approach to the management of the disease may be required. For example, a drug that effects the expression of enzymes that degrade the extracellular matrix of the optic nerve head would not likely prevent RGC death caused by excitotoxicity. In glaucoma, RGC death occurs by a process called apoptosis (programmed cell death). It has been speculated that different types of insults that can cause death may do so by converging on a few common pathways. Targeting downstream at a common pathway is a strategy that may broaden the utility of a drug and increase the probability that it may have utility in the management of different forms of the disease. However, drugs that effect multiple metabolic pathways are more likely to produce undesirable side-effects. With the advent of gene-based diagnostic kits to identify specific forms of glaucoma, selective neuroprotective agents can be tested with the aim of reducing the degree of variation about the measured response.

Glaucoma is currently diagnosed based on specific signs of the disease (characteristic optic nerve head changes and visual field loss). However, over half of the population with glaucoma are unaware they have this blinding disease and by the time they are diagnosed, they already have irreversibly lost approximately 30-50% of their retinal ganglion cells. Thus, improved methods for early diagnosis of glaucoma are needed.

Current glaucoma therapy is directed to lowering IOP, a major risk factor for the development and progression of glaucoma. However, none of the current IOP lowering therapies actually intervenes in the glaucomatous disease process responsible for elevated IOP and progressive damage to the anterior segment continues. This is one possible reason why most patients become "resistant" to conventional glaucoma therapies. Thus, what is needed is a therapeutic method for altering (by inhibiting or even reversing) the disease process.

SUMMARY OF THE INVENTION

The present invention overcomes these and other drawbacks of the prior art by providing methods to diagnose and compositions to treat glaucoma. In one aspect, the present invention provides a method for treating glaucoma by administering to a patient in need thereof a therapeutically effective amount of a composition comprising an agent that interacts with a gene encoding serum amyloid A protein (SAA), or with the gene's promoter sequence. The interaction between the agent and the gene encoding SAA, or with its promoter sequence, modulates the expression of SAA, such that the patient's glaucomatous condition is treated. In preferred embodiments, the agent will be a protein, peptide, peptidomimetic, small molecule or nucleic acid.

In another aspect, the present invention provides a method for treating glaucoma by administering to a patient in need thereof a therapeutically effective amount of a composition comprising an agent that inhibits interaction of the serum amyloid A protein (SAA) with its receptor. Preferably, the agent will be a peroxisome proliferator-activated receptor α (PPARα) agonists, tachykinin peptides and their non-peptide analogs or α-lipoic acid. Most preferably, the agent will be fenofibrate, Wy-14643, (4-chloro-6-(2,3-xylidino)-2-pryrimidinylthiol)-acetic acid), ciprofibrate, 2-bromohexadecanoic acid, bezafibrate and ciglitizone, bafilomycin, concanamycin or pseudolaric acid B.

The present invention further provides a pharmaceutical composition for treating glaucoma comprising a therapeutically effective amount of a serum amyloid A protein (SAA) antagonist and a pharmaceutical carrier. The antagonist contained in the composition may be any of the compounds identified above.

In yet another embodiment, the present invention provides a method for diagnosing glaucoma, by the following steps:
a) obtaining a biological sample from a patient; and
b) analyzing said sample for an aberrant level, aberrant bioactivity or mutations of the gene encoding serum amyloid A protein (SAA) or its promoter region or its gene products, wherein said gene encoding SAA comprises the sequence set forth in SEQ ID NO:1 or SEQ ID NO:3, wherein its promoter region comprises the sequence set forth in SEQ ID NO:12 or SEQ ID NO:13, and wherein SAA comprises the sequence set forth in SEQ ID NO:2 or SEQ ID NO:4;
wherein the aberrantly high level, aberrantly high bioactivity or mutations of the SAA genes or the gene products indicates a diagnosis of glaucoma.

In preferred aspects, the biological sample is ocular tissue, tears, aqueous humor, cerebrospinal fluid, nasal or cheek swab or serum. Most preferably, the biological sample comprises trabecular meshwork cells.

Alternatively, the present invention provides a method for diagnosing glaucoma in is a patient, by the steps:
a) collecting cells from a patient;
b) isolating nucleic acid from the cells;
c) contacting the sample with one or more primers which specifically hybridize 5' and 3' to at least one allele of SEQ ID NO:1, SEQ ID NO:3, SEQ ID NO:12, or SEQ ID NO:13 under conditions such that hybridization and amplification of the allele occurs; and
d) detecting the amplification product;

wherein aberrant level or mutations of SEQ ID NO:1, SEQ ID NO:3, SEQ ID NO:12, or SEQ ID NO:13, in the sample indicates a diagnosis of glaucoma.

The present invention also provides a method for identifying agents potentially useful for treating glaucoma, by the steps:
a) obtaining cells expressing SAA (SEQ ID NO:1 or SEQ ID NO:2) or cells containing SAA promoter/reporter gene such that the reporter gene is expressed;
b) admixing a candidate substance with the cells; and
c) determining the level of SAA protein (SEQ ID NO:2 or SEQ ID NO:4) or the level of gene expression in the cells;
wherein an increase or decrease of the production of SAA protein or gene expression in the presence of said candidate substance indicates an agent potentially useful for the treatment of glaucoma.

In another aspect, the present invention provides a method for identifying an agent potentially useful for treating glaucoma, by the steps:
a) forming a reaction mixture comprising:
(i) an SAA protein or a cell expressing SAA or a reporter gene driven by an SAA promoter;
(ii) an SAA protein binding partner; and
(iii) a test compound; and
b) detecting interaction of the SAA protein and binding partner or level of reporter gene products in the presence of the test compound and in the absence of the test compound;
wherein a decrease or increase in the interaction of the SAA protein with its binding partner in the presence of the test compound relative to the interaction in the absence of the test compound indicates a potentially useful agent for treating glaucoma.

In another aspect, the present invention provides a method for identifying an agent potentially useful for treating glaucoma, by the steps:
a) forming a reaction mixture comprising:
(i) cells comprising SAA recombinant protein (SEQ ID NO:2 or SEQ ID NO:4) or cells comprising expression vectors comprising SEQ ID NO:1 or SEQ ID NO:3; and
(ii) a test compound; and
b) detecting the effect on downstream signalling (IL-8) in the presence of the test compound and in the absence of the test compound;

wherein a decrease or increase in the downstream signalling in the presence of the test compound relative to the interaction in the absense of the test compound indicates a potentially useful agent for treating glaucoma.

In preferred aspects, the cells containing the SAA protein or expression vectors will be HL-60 cells.

BRIEF DESCRIPTION OF THE DRAWINGS

The following drawings form part of the present specification and are included to further demonstrate certain aspects of the present invention. The invention may be better understood by reference to these drawings in combination with the detailed description of specific embodiments presented herein.

DETAILED DESCRIPTION PREFERRED EMBODIMENTS

Figure 1:
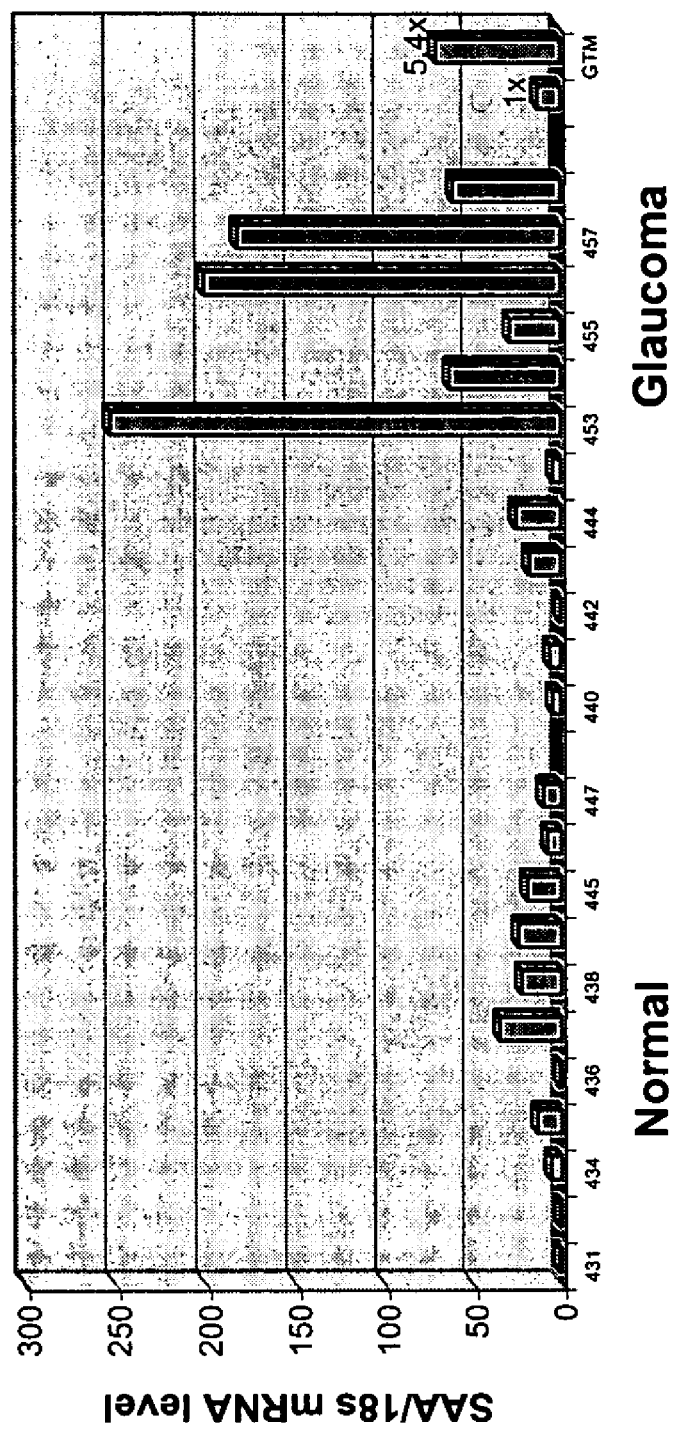
FIG. 1. QPCR analysis of SAA expression in 12 glaucoma vs. 11 normal TM tissues. NTM and GTM represent average expression level of the gene in normal and glaucoma groups, respectively.

Glaucoma is a heterogeneous group of optic neuropathies that share certain clinical features. The loss of vision in glaucoma is due to the selective death of retinal ganglion cells in the neural retina that is clinically diagnosed by characteristic changes in the visual field, nerve fiber layer defects, and a progressive cupping of the ONH. One of the main risk factors for the development of glaucoma is the presence of ocular hypertension (elevated intraocular pressure, IOP). IOP also appears to be involved in the pathogenesis of normal tension glaucoma where patients have what is often considered to be normal IOP. The elevated IOP associated with glaucoma is due to elevated aqueous humor outflow resistance in the trabecular meshwork (TM), a small specialized tissue located in the iris-corneal angle of the ocular anterior chamber. Glaucomatous changes to the TM include a loss in TM cells and the deposition and accumulation of extracellular debris including proteinaceous plaque-like material. In addition, there are also changes that occur in the glaucomatous optic nerve head (ONH). In glaucomatous eyes, there are morphological and mobility changes in ONH glial cells. In response to elevated IOP and/or transient ischemic insults, there is a change in the composition of the ONH extracellular matrix and alterations in the glial cell and retinal ganglion cell axon morphologies.

The present inventors have discovered that the expression of Serum Amyloid A (SAA) mRNA and protein are significantly upregulated in glaucomatous TM tissues and cells. The inventors have verified the differential mRNA expression seen using Affymetrix gene chips by real time quantitative polymerase chain reaction (QPCR) and increased SAA protein levels by SAA ELISA. This is the first time SAA has been shown to be expressed in the TM.

Human SAA comprises a number of small, differentially expressed apolipoproteins encoded by genes localized on the short arm of chromosome 11. There are four isoforms of SAAs. SAA1 (SEQ ID NO:2), encoded by SEQ ID NO:1, and SAA2 (SEQ ID NO:4), encoded by SEQ ID NO:3, are known as acute phase reactants, like C-reactive protein, that is, they are dramatically upregulated by proinflammatory cytokines. The 5'UTR promoter regions of SAA1 and SAA2 genes are also provided (SEQ ID NO:12 and SEQ ID NO:13, respectively). SAA3 (SEQ ID NO:5) is a pseudogene and SAA4 (SEQ ID NO:6) is a low level constitutively expressed gene encoding constitutive SAA4 (SEQ ID NO:7). SAA2 has two isoforms, SAA2α (SEQ ID NO:9), encoded by SEQ ID NO:8, and SAA2β (SEQ ID NO:11), encoded by SEQ ID NO:10, which differ by only one amino acid. SAA1 and SAA2 proteins are 93.5% identical at the amino acid level (SEQ ID NO:2 and SEQ ID NO:4, respectively) and these genes are 96.7% identical at the nucleotide level (SEQ ID NO:1 and SEQ ID NO:3, respectively).

SAA is an acute-phase reactant whose level in the blood is elevated approximately is 1000-fold as part of the body's responses to various injuries, including trauma, infection, inflammation, and neoplasia. As an acute-phase reactant, the liver has been considered to be the primary site of expression. However, extrahepatic SAA expression was described initially in mouse tissues, and later in cells of human atherosclerotic lesions (O'Hara et al. 2000). Subsequently, SAA mRNA was found widely expressed in many histologically normal human tissues. Localized expression was noted in a variety of tissues, including breast, stomach, small and large intestine, prostate, lung, pancreas, kidney, tonsil, thyroid, pituitary, placenta, skin epidermis, and brain neurons. Expression was also observed in lymphocytes, plasma cells, and endothelial cells. SAA protein expression co-localized with SAA mRNA expression has also been reported in histologically normal human extrahepatic tissues. (Liang et al. 1997; Urieli-Shoval et al. 1998).

SAA isoforms are apolipoproteins that become a major component of high-density lipoprotein (HDL) in the blood plasma of mammals and displaces A-I (ApoA-I) and phospholipid from the HDL particles (Miida et al. 1999). SAA binds cholesterol and may serve as a transient cholesterol-binding protein. In addition, over-expression of SAA1 or SAA2 leads to the formation of linear fibrils in amyloid deposits, which can lead to pathogenesis (Uhlar and Whitehead 1999; Liang et al. 1997). SAA plays an important role in infections, inflammation, and in the stimulation of tissue repair. SAA concentration may increase up to 1000-fold following inflammation, infection, necrosis, and decline rapidly following recovery. Thus, serum SAA concentration is considered to be a useful marker with which to monitor inflammatory disease activity. Hepatic biosynthesis of SAA is up-regulated by pro-inflammatory cytokines, leading to an acute phase response. Chronically elevated SAA concentrations are a prerequisite for the pathogenesis of secondary amyloidosis, a progressive and sometimes fatal disease characterized by the deposition in major organs of insoluble plaques composed principally of proteolytically cleaved SAA. This same process also may lead to atherosclerosis. There is a requirement for both positive and negative SAA control mechanisms to maintain homeostasis. These mechanisms permit the rapid induction of SAA expression to fulfill host-protective functions, but they also must ensure that SAA expression is rapidly returned to baseline levels to prevent amyloidosis. These mechanisms include modulation of promoter activity involving, for example, the inducer nuclear factor kB (NF-kB) and its inhibitor IkB, up-regulation of transcription factors of the nuclear factor for interleukin-6 (NF-IL6) family, and transcriptional repressors such as yin and yang 1 (YY1). Post-transcriptional modulation involving changes in mRNA stability and translation efficiency permit further up- and down-regulatory control of SAA protein synthesis to be achieved. In the later stages of the AP response, SAA expression is effectively down-regulated via the increased production of cytokine antagonists such as the interleukin-1 receptor antagonist (IL-1Ra) and of soluble cytokine receptors, resulting in less signal transduction driven by pro-inflammatory cytokines (Jensen and Whitehead 1998).

There are several reports suggesting that primary amyloidosis may be associated with glaucoma. For example, it was found that amyloid was deposited in various ocular tissues including the vitreous, retina, choroid, iris, lens, and TM in primary systemic amyloidosis patients (Schwartz et al. 1982). Ermilov et al. (1993) reported that in 478 eyes of 313 patients, aged 25 years to 90 years, with cataracts, glaucoma, and/or diabetes mellitus, 66 (14%) of the eyes contained amyloid-pseudoexfoliative amyloid (PEA). Krasnov et al. (1996) reported that 44.4% of 115 patients with open-angle glaucoma revealed extracellular depositions of amyloid. Amyloidosis was revealed in the sclera in 82% of the cases and in the iris in 70% of the cases. A number of clinical conditions, including Alzheimer's disease, exhibit aberrant amyloid tissue deposits associated with disease. However, amyloids are molecularly heterogeneous and encoded by different amyloid genes. The previous reports are unclear regarding which amyloid(s) might be associated with glaucoma. The present inventors have shown, for the first time, that SAA gene expression is elevated significantly in glaucomatous TM tissues. Increased SAA may be involved in the generation of elevated IOP and damage to the optic nerve leading to vision loss in glaucoma patients. The present invention provides methods of using a finding of increased SAA expression to diagnose glaucoma. The present invention further provides methods for screening for agents that alter SAA expression or function in order to identify potentially anti-glaucomatous agents. In another aspect, the present invention provides methods and compositions of using agents that antagonize SAA actions and/or interactions with other proteins for the treatment of glaucoma.

Diagnosing Glaucoma

Based on the inventors' finding that certain subjects with glaucoma have increased levels of SAA expression, the present invention provides a variety of methods for diagnosing glaucoma. Certain methods of the invention can detect mutations in nucleic acid sequences that result in inappropriately high levels of SAA protein. These diagnostics can be developed based on the known nucleic acid sequence of human SAA, or the encoded amino acid sequence (see Miller 2001). Other methods can be developed based on the genomic sequence of human SAA or of the sequence of genes that regulate expression of SAA. Still other methods can be developed based upon a change in the level of SAA gene expression at the mRNA level.

In alternative embodiments, the methods of the invention can detect the activity or level of SAA signaling proteins or genes encoding SAA signaling proteins. For example, methods can be developed that detect inappropriately low SAA signaling activity, including for example, mutations that result in inappropriate functioning of SAA signaling components, including SAA induction of IL-8. In addition, non-nucleic acid based techniques may be used to detect alteration in the amount or specific activity of any of these SAA signaling proteins.

A variety of means are currently available to the skilled artisan for detecting aberrant levels or activities of genes and gene products. These methods are well known by and have become routine for the skilled artisan. For example, many methods are available for detecting specific alleles at human polymorphic loci. The preferred method for detecting a specific polymorphic allele will depend, in part, upon the molecular nature of the polymorphism. The various allelic forms of the polymorphic locus may differ by a single base-pair of the DNA. Such single nucleotide polymorphisms (or SNPs) are major contributors to genetic variation, comprising some 80% of all known polymorphisms, and their density in the human genome is estimated to be on average 1 per 1,000 base pairs. A variety of methods are available for detecting the presence of a particular single nucleotide polymorphic allele in an individual. Advancements in the field have provided accurate, easy, and inexpensive large-scale SNP genotyping. For example, see U.S. Pat. No. 4,656,127; French Patent 2,650,840; PCT App. No. WO91/02087; PCT App. No. WO92/15712; Komher et al. 1989; Sokolov 1990; Syvanen et al. 1990; Kuppuswamy et al. 1991; Prezant et al. 1992; Ugozzoli et al. 1992; Nyren et al. 1993; Roest et al. 1993; and van der Luijt et al. 1994).

Any cell type or tissue may be utilized to obtain nucleic acid samples for use in the diagnostics described herein. In a preferred embodiment, the DNA sample is obtained from a bodily fluid, e.g., blood, obtained by known techniques (e.g. venipuncture), or buccal cells. Most preferably, the samples for use in the methods of the present invention will be obtained from blood or buccal cells. Alternately, nucleic acid tests can be performed on dry samples (e.g. hair or skin).

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo 1992).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

A preferred detection method is allele specific hybridization using probes overlapping a region of at least one allele of an SAA signaling component that is indicative of glaucoma and having about 5, 10, 20, 25 or 30 contiguous nucleotides around the mutation or polymorphic region. In a preferred embodiment of the invention, several probes capable of hybridizing specifically to other allelic variants involved in glaucoma are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al. (1996). In one embodiment, a chip comprises all the allelic variants of at least one polymorphic region of a gene. The solid phase support is then contacted with a test nucleic acid and hybridication to the specific probes is detected. Accordingly, the identity of numerous allelic variants of one or more genes can be identified in a simple hybridization experiment.

These techniques may further include the step of amplifying the nucleic acid before analysis. Amplification techniques are known to those of skill in the art and include, but are not limited to, cloning, polymerase chain reaction (PCR), polymerase chain reaction of specific alleles (ASA), ligase chain reaction (LCR), nested polymerase chain reaction, self sustained sequence replication (Guatelli et al. 1990), transcriptional amplification system (Kwoh et al. 1989), and Q-Beta Replicase (Lizardi, et al. 1988).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, SSCP, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize 5' and 3' to at least one allele of SAA that is indicative of glaucoma under conditions such that hybridization and amplification of the allele occurs, and (iv) detecting the amplification product. These detection schemes are especially useful for the detection of nucleic acid molecules if such molecules are present in very low numbers.

In a preferred embodiment of the subject assay, aberrant levels or activities of SAA that are indicative of glaucoma are identified by alterations in restriction enzyme cleavage patterns. For example, sample and control DNA is isolated, amplified (optionally), digested with one or more restriction endonucleases, and fragment length sizes are determined by gel electrophoresis.

In yet another embodiment, any of a variety of sequencing reactions known in the art can be used to directly sequence the allele. Exemplary sequencing reactions include those based on techniques developed my Maxim and Gilbert (1977) or Sanger (1977). It is also contemplated that any of a variety of automated sequencing procedures may be utilized when performing the subject assays, including sequencing by mass spectrometry (see, for example WO94/16101; Cohen et al. 1996; Griffin et al. 1993). It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamin or osmium tetraoxide and with piperidine) can be used to detect mismatched bases in RNA/RNA or RNA/DNA or DNA/DNA heteroduplexes (Myers et al. 1985b; Cotton et al. 1988; Saleeba et al. 1992). In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of *E. coli* cleaves A at G/A mismatches and the thymidine DNA glycosylase from HeLa cells cleaves T and G/T mismatches (Hsu et al. 1994; U.S. Pat. No. 5,459,039).

In other embodiments, alterations in electrophoretic mobility will be used to identify aberrant levels or activities of SAA that are indicative of glaucoma. For example, single strand conformation polymorphism (SSCP) may be used to detect differences in electrophoretic mobility between mutant and wild type nucleic acids (Orita et al. 1989; Cotton 1993; Hayashi 1992; Keen et al. 1991).

In yet another embodiment, the movement of alleles in polyacrylamide gels containing a gradient of denaturant is assayed using denaturing gradient gel electrophoresis (DGGE) (Myers et al. 1985a). In a further embodiment, a temperature gradient is used in place of a denaturing agent gradient to identify differences in the mobility of control and sample DNA (Rosenbaum and Reissner 1987).

Examples of other techniques for detecting alleles include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. 1986; Saiki et al. 1989). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al. 1989) or at the extreme 3' end of one primer where, under appropriate conditions, mismatch can prevent, or reduce polymerase extension (Prossner 1993). In addition it may be desirable to introduce a novel restriction site in the region of the mutation to create cleavage-based detection (Gasparini et al. 1992). It is anticipated that in certain embodiments amplification may also be performed using Taq ligase for amplification (Barany 1991). In such cases, ligation will occur only if there is a perfect match at the 3' end of the 5' sequence making it possible to detect the presence of a known mutation at a specific site by looking for the presence or absence of amplification.

In another embodiment, identification of an allelic variant is carried out using an oligonucleotide ligation assay (OLA), as described, E.g., in U.S. Pat. No. 4,998,617 and in Landegren et al. 1988). Nickerson et al. have described a nucleic acid detection assay that combines attributes of PCR and OLA (Nickerson et al. 1990). In this method, PCR is used to achieve the exponential amplification of target DNA, which is then detected using OLA.

Several techniques based on this OLA method have been developed and can be used to detect aberrant levels or activities of SAA that are indicative of glaucoma. For example, U.S. Pat. No. 5,593,826 and Tobe et al. (1996), describe such techniques that are frequently used.

In one embodiment, fenofibrate, a peroxisome proliferator-activated receptor α (PPARα) agonist, may be formulated in a pharmaceutically acceptable composition and used to treat glaucoma by modulating SAA expression. Studies have shown that fenofibrate and WY 14643 treatment reduces plasma SAA concentration (Yamazaki et al. 2002). It is believed that other PPARα agonists, such as ciprofibrate, 2-bromohexadecanoic acid, bezafibrate, ciprofibrate and ciglitizone may also be useful for the treatment of glaucoma.

The present inventors further postulate that agents that prevent amyloid-induced cell death may be useful for protecting TM and other ocular cells in the anterior uvea and at the back of the eye, especially the retina and optic nerve head.

The Compounds of this invention, can be incorporated into various types of ophthalmic formulations for delivery to the eye (e.g., topically, intracamerally, or via an implant). The Compounds are preferably incorporated into topical ophthalmic formulations for delivery to the eye. The Compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a Compound in a physiologically acceptable isotonic aqueous buffer. Further, the ophthalmic solution may include an ophthalmologically acceptable surfactant to assist in dissolving the Compound. Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the Compound in a hydrophilic base prepared from the combination of, for example, carbopol-974, or the like, according to the published formulations for analogous ophthalmic preparations; preservatives and tonicity agents can be incorporated.

The Compounds are preferably formulated as topical ophthalmic suspensions or solutions, with a pH of about 4 to 8. The establishment of a specific dosage regimen for each individual is left to the discretion of the clinicians. The Compounds will normally be contained in these formulations in an amount 0.01% to 5% by weight, but preferably in an amount of 0.05% to 2% and most preferably in an amount 0.1 to 1.0% by weight. The dosage form may be a solution, suspension microemulsion. Thus, for topical presentation 1 to 2 drops of these formulations would be delivered to the surface of the eye 1 to 4 times per day according to the discretion of a skilled clinician.

The Compounds can also be used in combination with other agents for treating glaucoma, such as, but not limited to, β-blockers, prostaglandins, carbonic anhydrase inhibitors, $\alpha_2$ agonists, miotics, and neuroprotectants.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Increased Expression of SAA1 and SAA2 in Glaucomatous TM Cells and Tissues

Figure 2A:
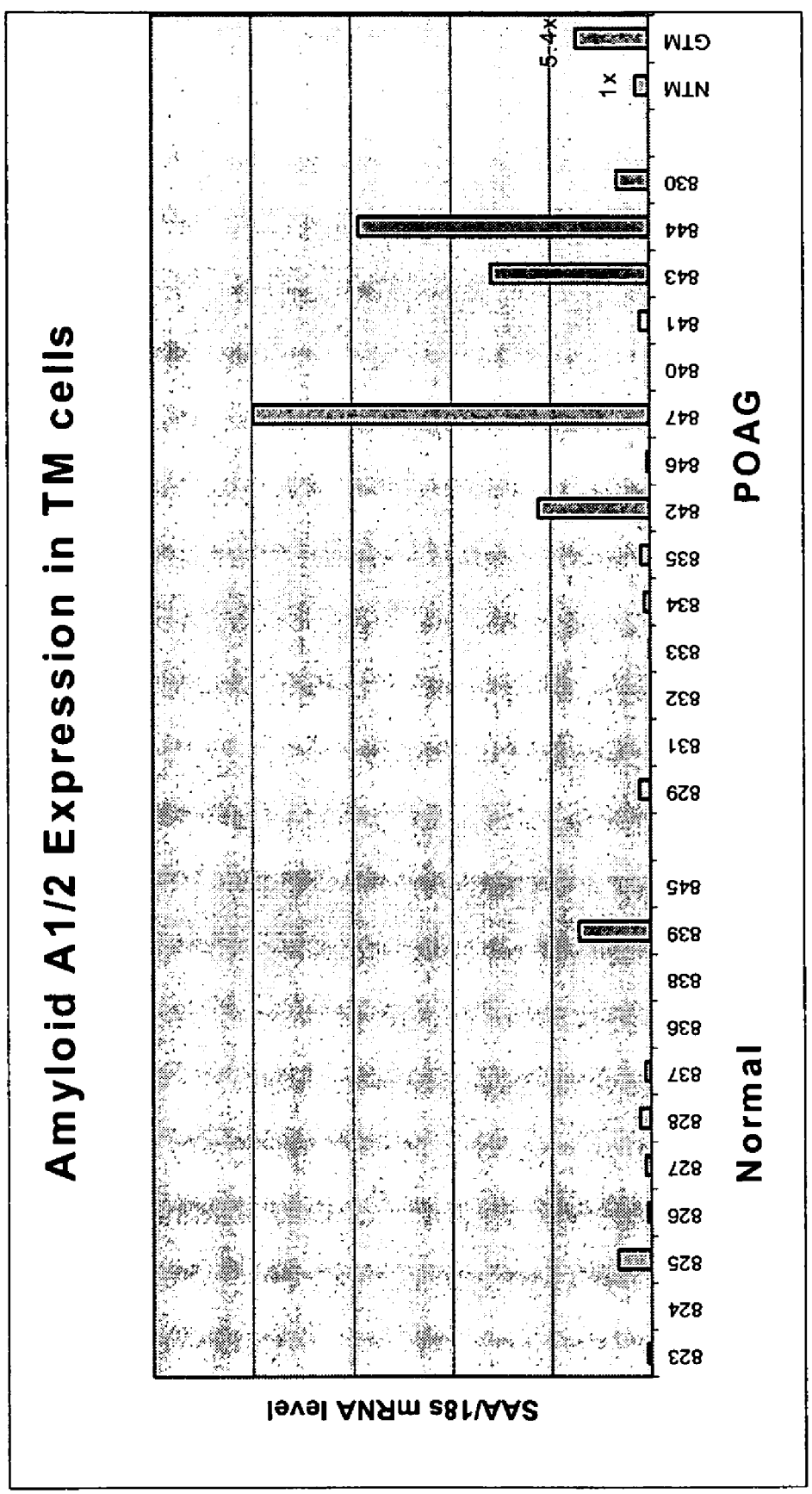
FIG. 2A. QPCR analysis of SAA expression in TM cell lines. NTM and GTM represent average expression level of the gene in normal and glaucoma groups, respectively.
Figure 2B:
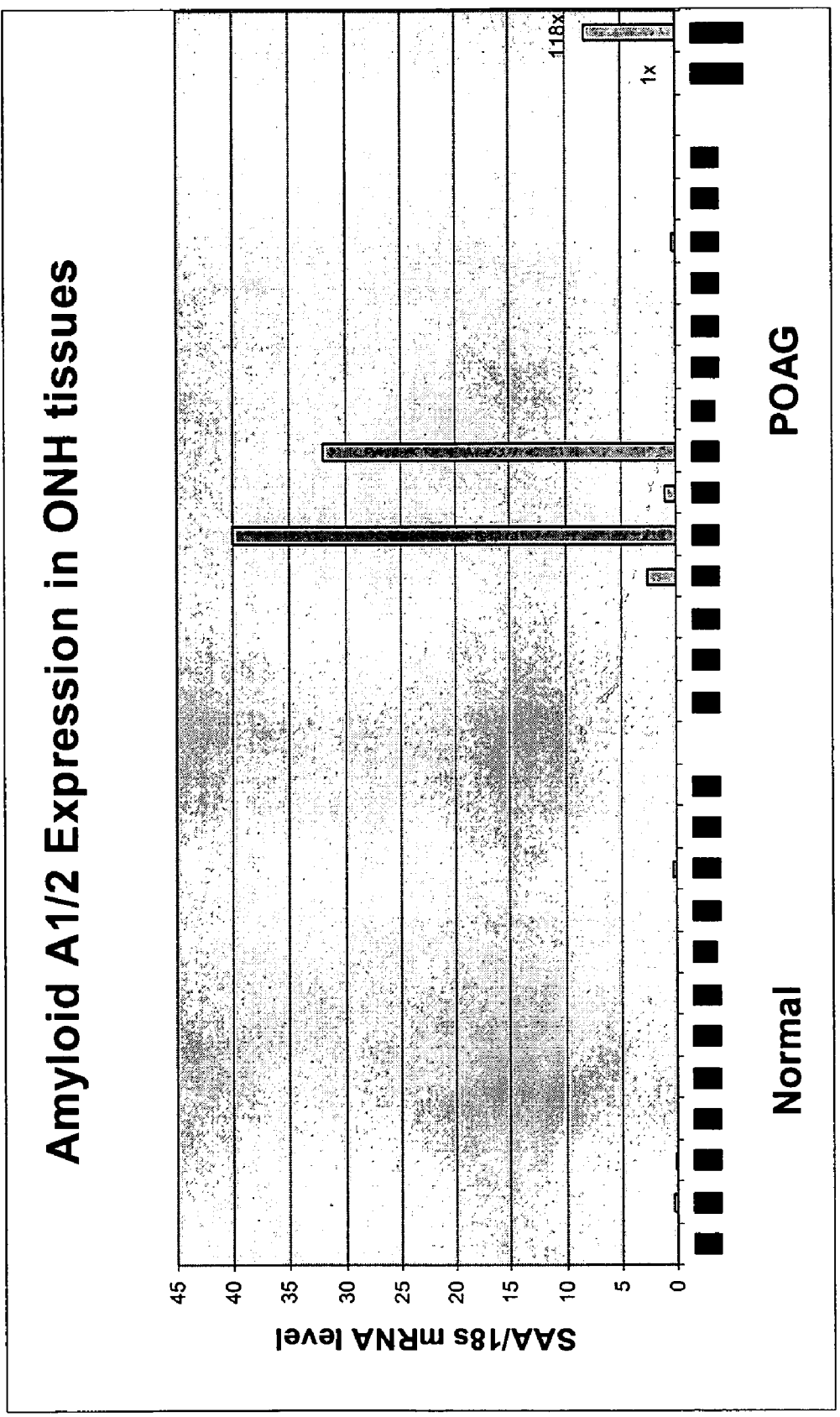
FIG. 2B. QPCR analysis of SAA expression in optic nerve head tissues. NTM and GTM represent average expression level of the gene in normal and glaucoma groups, respectively.
Figure 3:
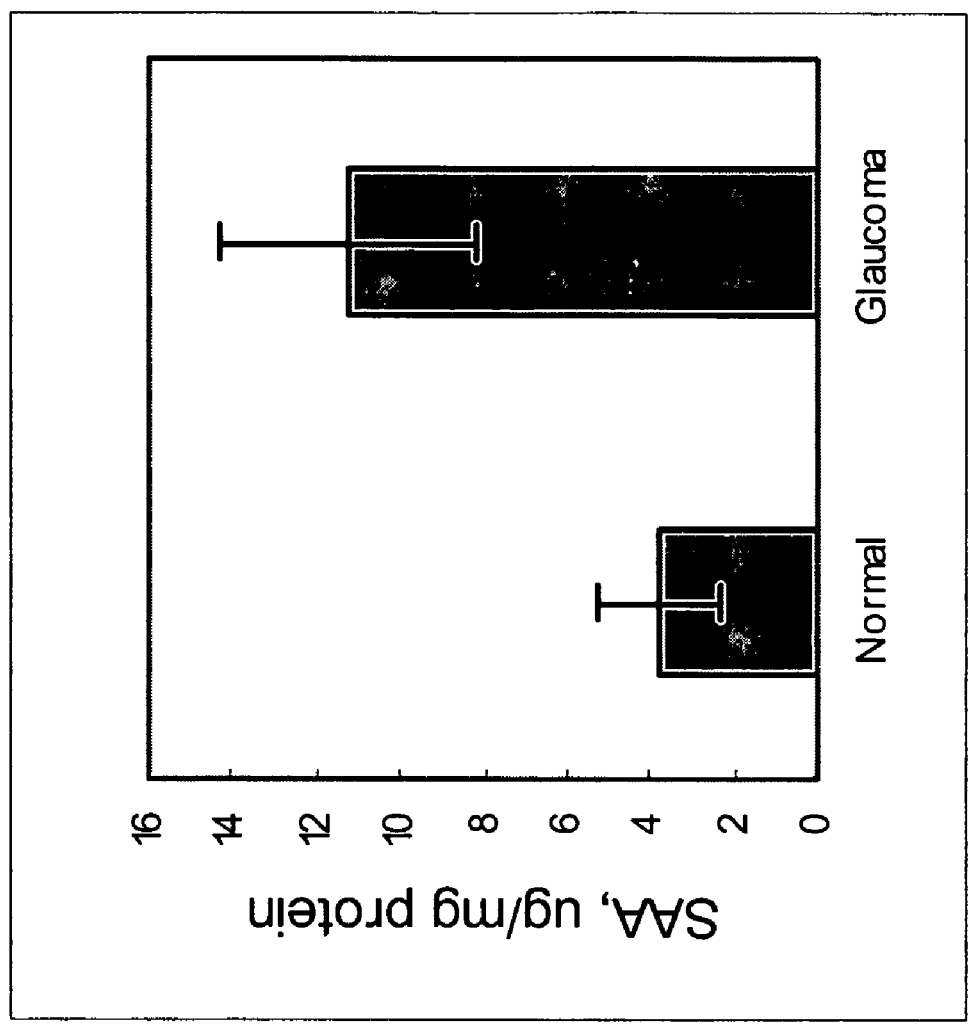
FIG. 3. SAA protein in TM tissues from normal and glaucoma donors (n=6). A significant increase (3-fold) in SAA was observed in glaucoma TM tissues compared to normal tissue (p=0.031). The bars show mean+/−s.e.m.

RNA pools of TM tissues from 13 normal donors vs. 9 glaucoma donors was used to determine gene expression using the Affymetric GeneChips set (HG-U133). Amyloid A2 expression was identified to increase 4 fold in glaucoma comparing to that in normal TM tissues. To confirm this result, QPCR was conducted using individual RNA from 12 glaucoma and 11 normal TM tissues. Five from 12 glaucoma TM tissues (42%) showed significant increase in SAA1/2 expression. Average of SAA expression in the 12 glaucoma TM was 5.4 fold to that in the 11 normal TM (FIG. 1). In addition, a similar trend of SAA differential expression was observed in glaucoma TM cells or glaucoma optic nerve head tissues. There was an average increase of 5.4-fold in glaucoma TM cells (14 glaucoma vs. 11 normal TM cell lines, FIG. 2A) and 118-fold in glaucoma optic nerve head tissues (14 glaucoma vs. 12 normal, FIG. 2B) compared to normals, respectively. ELISA of SAA in TM tissues from 6 normal and 6 glaucoma donors showed that SAA protein was also significantly increased in glaucoma TM tissues compared to normals. There was a 3-fold difference in SAA concentration in glaucomatous tissue compared to normal tissue (11.3 and 3.8 µg/mg protein respectively). These data are shown in FIG. 3.

Figure 4:
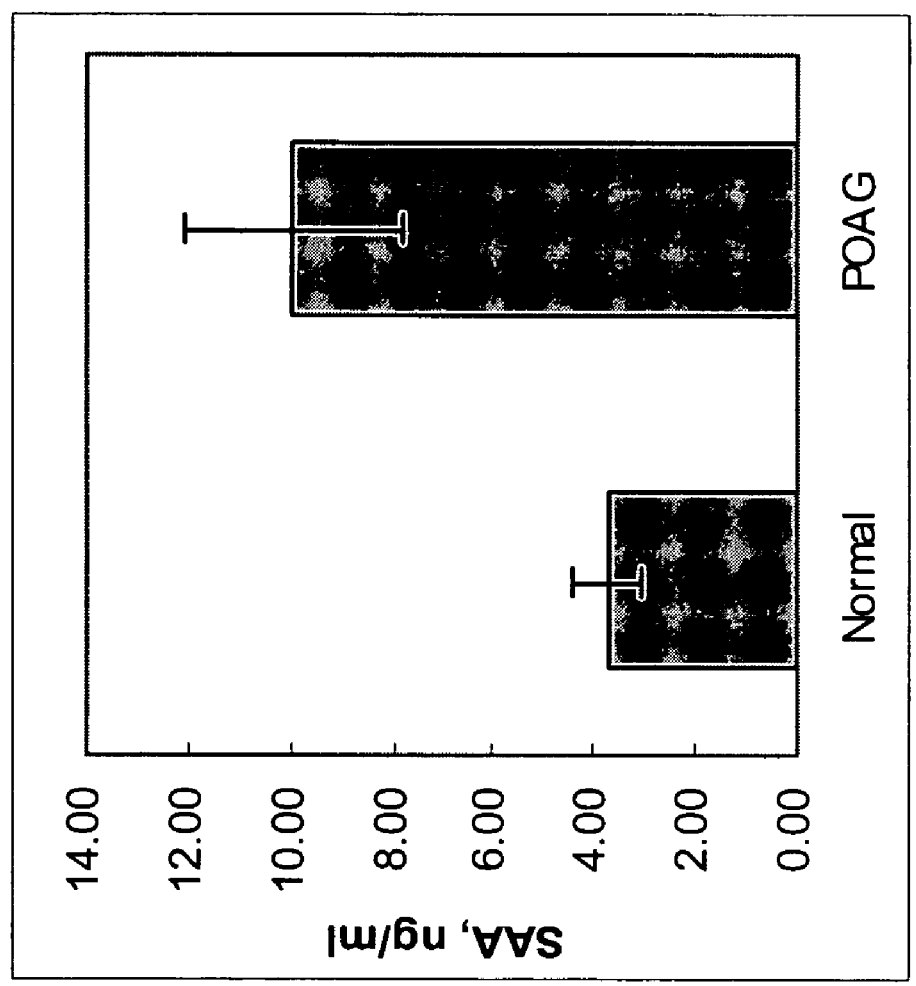
FIG. 4. SAA protein determined by ELISA in human aqueous humor from normal and glaucomatous individuals. The values are expressed as the average SAA in ng/ml of aqueous humor, +/−s.e.m. (p=0.005).

An association of increased expression of SAA with glaucoma was further demonstrated in human aqueous humor. SAA protein was measured by ELISA in aqueous humor from 16 normal and 20 glaucomatous individuals. SAA was found to be almost 3 times higher in glaucomatous aqueous humor than in normal samples (10.0 ng/ml vs. 3.7 ng/ml respectively). The results are shown in FIG. 4.

EXAMPLE 2

Formulation of Fenofibrate for Topical Application

1% Fenofibrate suspension for topical application to decrease SAA and lower IOP in the eye.

| Description | Conc. | Units | Purpose |
|---|---|---|---|
| Fenofibrate (AL18543), NOC | 1% | W/V % | active ingredient |
| hydroxypropyl methylcellulose | 0.5% | W/V % | viscosity modifier (2910) (E4M), USP |
| dibasic sodium phosphate | 0.2% | W/V % | buffering agent (anhydrous), usp |
| sodium chloride, usp | 0.75% | W/V % | tonicity agent |
| disodium edta | 0.01% | W/V % | chelating agent (edetate disodium), usp |
| polysorbate 80, nf | 0.05% | W/V % | wetting agent |
| benzalkonium chloride, nf | 0.01% | W/V % | preservative |
| sodium hydroxide, nf | q.s. pH | W/V % | pH adjust |
| hydrochloric acid, nf | q.s. pH | W/V % | pH adjust |
| purified water, usp | q.s. 100% | W/V % | vehicle |

EXAMPLE 3

Procedure for Screening and Identifying Compounds that Alter the Expression of SAA mRNA or SAA Proteins One method that can be used for screening for agents that alter SAA expression and function is to determine changes in SAA protein levels. Kits for in vitro assay for quantitative determination of Serum Amyloid A (SAA) in animal or human sera, plasma, buffered solutions, cell culture media, and tissue or cell extracts are commercially available. The assay is a solid phase sandwich Enzyme Linked-Immuno-Sorbent Assay (ELISA). A monoclonal antibody specific for SAA has been coated onto the wells of a microtiter plate. Samples, including standards of known SAA content, or unknowns, are added to these wells along with a secondary antibody conjugated to alkaline phosphatase or peroxidase. The antibodies are constructed such that neither one interferes with the binding epitope of the other. The SAA is both captured on the plate by the immobilized antibody and labeled with the conjugated second antibody in a one step procedure. After an incubation period, the plate is washed to remove all unbound material and a substrate (PNPP or peroxide) is added. The intensity of the colored product is proportional to the concentration of SAA present in the unknown sample.

EXAMPLE 4

Induction of SAA in Cultured Cell Lines for Screening Compounds that Alter the Expression of SAA mRNA or Protein The human hepatoma cell line, HepG2, is widely used for studies on SAA induction by cytokines, for transfection with plasmids, and reporter assays. SAA mRNA and protein synthesis can be induced by various cytokines in several human hepatoma cell lines including PCL/PRF/5, HepB and HepG2 (Uhlar and Whitehead 1999). SAA synthesis by human aortic smooth muscle cells (HASMC) is induced by glucocorticoid hormones and not by the proinflammatory cytokines, IL-1, IL-6, and TNF-α, which stimulate the production of SAA by hepatocytes (Kumon et al. 2002b;

Kumon et al. 2001; Thorn and Whitehead 2002). SAA stimulated the chemotactic migration of HASMC in a dose dependent manner when assayed using a Chemotaxicell culture chamber (Kumon et al. 2002a). SAA mRNA expression and protein production was demonstrated in primary cultures of rheumatoid arthritis synoviocytes (O'Hara et al. 2000).

EXAMPLE 5

Functional Analysis of SAA in Cultured Cells

Figure 5:
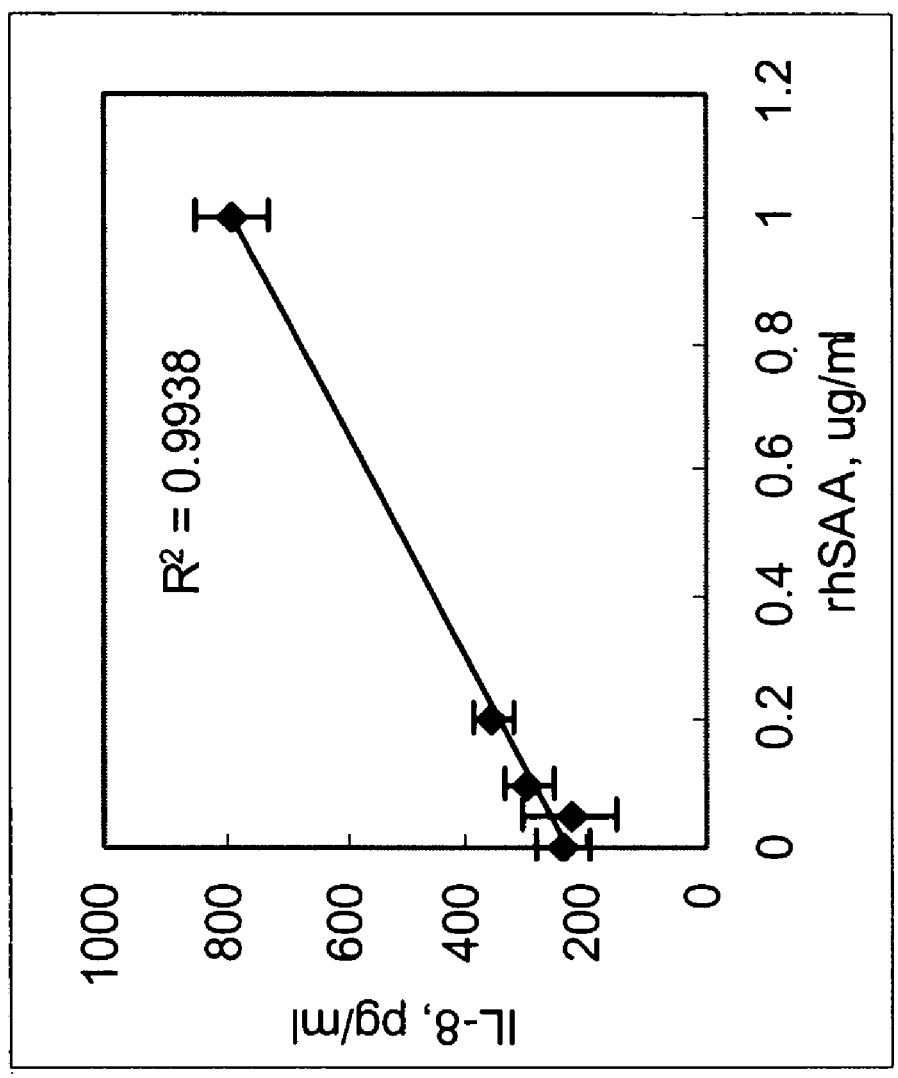
FIG. 5. IL-8 secretion by HL-60 cells in response to increasing concentrations of rhSAA.

Cytokine-like properties of SAA include induction of IL-8 secretion by neutrophils. (Furlaneto and Campa, 2002; He et al. 2003). HL-60 cells, a promyelocytic cell line, was identified that responds to SAA with increased IL-8 secretion, and can be used for in vitro assays of SAA function. HL-60 cells were treated for four hours with increasing concentrations of recombinant human SAA, and IL-8 was measured in the media by ELISA. IL-8 secretion increased in a dose dependent manner (FIG. 5). HL-60 cells can be used as a surrogate cell line for functional assays to identify agents that alter SAA function and expression levels.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

United States Patents
Books
Other Publications

Furlenato, C J, and Campa A, *A novel function of serum amyloid A: a potent stimulus for the release of tumor necrosis factor-alpha, interleukin-1 beta, and interleukin-8 by human blood neutrophil*, BIOCHEM. BIOPHYS. RES. COMMUN 268:405-408 (2002).

He, R, Sang H, Ye, R D, *Serum amyloid A induces IL-8 secretion through a G protein-coupled receptor, FPRL1/LXA4R*, BLOOD 101:1572-1581 (2003).

Jensen L E and Whitehead A S, BIOCHEM. J. 334:489-503 (1998).

Jordat M S, et al., PLANTA MED. 68:667-71 (2002).

Kane et al., J. NEUROCHEM., 72: 1939-1947 (1999).

Kumon, Y., Hosokawa, T., Suchiro, T., Ideda, Y., Sipe, J. D., and Hashimoto, K., *Acute-phase, but not constitutive serum amyloid A (SAA) is chemotactic for cultured human aortic smooth muscle cells*, AMYLOID 9:237-241 (2002a).

Kumon, Y., Suchiro, T., Faulkes, D. J., Hosakawa, T., Ideda, Y., Woo, P., Sipe, J. D., and Hashimoto, K., *Transcriptional regulation of Serum Amyloid A1 gene expression in human aortic smooth muscle cells involves CCAAT/enhancer binding proteins (C/EBP) and is distinct from HepG2 cells*, SCAND. J. IMMUNOL. 56:504-511 (2002b).

Kumon, Y., Suchiro, T., Hashimoto, K., and Sipe, J. D., *Dexamethasone, but not IL-1 alone, upregulates acute-phase serum amyloid A gene expression and production by cultured human aortic smooth muscle cells*, SCAND J. IMMUNOL. 53:7-12 (2001).

Lambert et al., PROC. NAT. ACAD. SCI. USA 95: 6448-6453 (1998).

Liang, J. S., Sloane, J. A., Wells, J. M., Abraham, C. R., Fine, R. E., and Sipe, J. D., *Evidence for local production of acute phase response apolipoprotein serum amyloid A in Alzheimer's disease brain*, NEUROSCI. LETT. 225:73-76 (1997).

Liu et al., J. NEUROCHEM. 69: 2285-2293 (1997).

Miida T., Yamada, T., Yamadera, T., Ozaki, K., Inano, K., Okada, M., *Serum amyloid A protein generates pre-beta 1 high-density lipoprotein from alpha-migrating high-density lipoprotein*, BIOCHEM. 38(51): 16958-16962 (1999).

Miller, Genome Biology 3(1):reviews 3001.1-3001.15 (2001).

Nakagami et al., EUR. J. PHARMACOL. 457: 11-17 (2002a).

Nakagami et al., BR. J. PHARMACOL., 137: 676-682 (2002b).

O'Hara, R., Murphy, E. P., Whitehead, A. S., FitzGerald, O., and Bresnihan, B., *Acute-phase serum amyloid A production by rheumatoid arthritis synovial tissue*, ARTHRITIS RES. 2:142-144 (2000).

Pike et al., J. NEUROSCI. 13: 1676-1687 (1993).

Thorn, C. F. and Whitehead, A. S., *Differential glucocorticoid enhancement of the cytokine-driven transcriptional activation of the human actue phase serum amyloid A genes, SAA1 and SAA*, J. IMMUNOL. 169:399-406 (2002).

Uhlar, C. M., and Whitehead, A. S., *Serum amyloid A, the major vertebrate acute-phase reactant*, EUR. J. BIOCHEM. 265:501-523 (1999).

Urieli-Shoval, S., Cohen, P., Eisenberg, S., and Matzner, Y., *Widespread expression of serum amyloid A in histologically normal human tissue. Predominant localization to the epithelium*, J. HISTOCHEM. CYTOCHEM. 46:1377-1384 (1998).

Yamazaki et al., BIOCHEMICAL AND BIOPHYSICAL RES. COMM., 290:1114-1122 (2002).

Yankner et al., SCIENCE 250: 279-282 (1990)

Zhang et al., NEUROSCI. LETT. 312: 125-128 (2001)

We claim:

1. A method for treating glaucoma, said method comprising administering to a patient in need thereof a therapeutically effective amount of a composition comprising a small molecule agent that interacts with a gene encoding serum amyloid A protein (SAA), wherein said small molecule agent is a peroxisome proliferator-activated receptor α(PPARa) agonist selected from the group consisting of fenofibrate, WY-14643, ciprofibrate, 2-bromohexadecanoic acid, bezafibrate, and ciglitizone, wherein said interaction modulates the expression of SAA, and wherein a decrease in expression of SAA treats glaucoma.

* * * * *

SEQUENCE LISTING

<160> NUMBER OF SEQ ID NOS: 13

<210> SEQ ID NO 1
<211> LENGTH: 369

```
<212> TYPE: DNA
<213> ORGANISM: homo sapiens

<400> SEQUENCE: 1
atgaagcttc tcacgggcct ggttttctgc tccttggtcc tgggtgtcag cagccgaagc      60 ttctttcgt tccttggcga ggcttttgat ggggctcggg acatgtggag agcctactct     120
gacatgagag aagccaatta catcggctca gacaaatact tccatgctcg gggaactat     180 gatgctgcca aaggggacc tgggggtgtc tgggctgcag aagcgatcag cgatgccaga     240
gagaatatcc agagattctt tggccatggt gcggaggact cgctggctga tcaggctgcc     300
aatgaatggg gcaggagtgg caaagacccc aatcacttcc gacctgctgg cctgcctgag     360
aaatactga                                                             369

<210> SEQ ID NO 2
<211> LENGTH: 122
<212> TYPE: PRT
<213> ORGANISM: homo sapiens

<400> SEQUENCE: 2

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Val Trp Ala Ala Glu Ala Ile Ser Asp Ala Arg
65                  70                  75                  80

Glu Asn Ile Gln Arg Phe Phe Gly His Gly Ala Glu Asp Ser Leu Ala
                85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
        115                 120

<210> SEQ ID NO 3
<211> LENGTH: 570
<212> TYPE: DNA
<213> ORGANISM: homo sapiens

<400> SEQUENCE: 3 agggaccccgc agctcagcta cagcacagat cagcaccatg aagcttctca cgggcctggt      60
tttctgctcc ttggtcctga gtgtcagcag ccgaagcttc ttttcgttcc ttggcgaggc     120
ttttgatggg gctcgggaca tgtggagagc ctactctgac atgagagaag ccaattacat     180
cggctcagac aaatacttcc atgctcgggg aactatgat gctgccaaaa ggggacctgg     240
gggtgcctgg gccgcagaag tgatcagcaa tgccagagag aatatccaga gactcacagg     300
ccatggtgcg gaggactcgc tggccgatca ggctgccaat aaatgggca ggagtggcag     360 agacccccaat cacttccgac ctgctggcct gcctgagaaa tactgagctt cctcttcact     420
ctgctctcag gagacctggc tatgaggccc tcggggcagg gatacaaagt tagtgaggtc     480
tatgtccaga gaagctgaga tatggcatat aataggcatc taataaatgc ttaagaggtc     540
aaaaaaaaaa aaaaaaaaaa aaaaaaaaaa                                      570
```

<210> SEQ ID NO 4
<211> LENGTH: 122
<212> TYPE: PRT
<213> ORGANISM: homo sapiens

<400> SEQUENCE: 4

Met Lys Leu Leu Thr Gly Leu Val Phe Cys Ser Leu Val Leu Ser Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Ala Trp Ala Ala Glu Val Ile Ser Asn Ala Arg
65                  70                  75                  80

Glu Asn Ile Gln Arg Leu Thr Gly His Gly Ala Glu Asp Ser Leu Ala
                85                  90                  95

Asp Gln Ala Ala Asn Lys Trp Gly Arg Ser Gly Arg Asp Pro Asn His
            100                 105                 110

Phe Arg Pro Ala Gly Leu Pro Glu Lys Tyr
        115                 120

<210> SEQ ID NO 5
<211> LENGTH: 4286
<212> TYPE: DNA
<213> ORGANISM: homo sapiens

<400> SEQUENCE: 5

```
gatggttgac aactcccctc ctcttccccc tcttctactg tctactcctg ggaccaagtg      60
agccacgcca gctcagatac tacactgacc acagggaatc ccaccttttc caaggaatgg    120
aagttgtgta gggaatattc aaatgttgct tagcattgcc ttagataaga accaaaggga    180
cagggaaatc ctctgacagc tatctgcctt ataactttca ttttactgtg cctaaaatat    240
gctcagaacc cagaaagagg cataattcct aattttggca ggctctaatc taaaataatg    300
attctcaaac atggtgtgac ttttgtctat ttgctttatc ctgggtcact gctcctcttc    360
tgtcagatac tgggattcca atgagacaaa tggaaatgga gacgtagacc ctctgacctt    420
ctatctttta tctatacaca tacacctgtg tgtgtgtgtg tgtgtgtgtg tgtgcgtgtg    480
taaaaccgag tgggtttttt tcttggaatg aaagaatgga ctaacattac aaaaaataaa    540
aacttgaaac agaatgtgta ttatccttgg ttgtgtttcc ttggccctgc agcaggatga    600
agctctccac tggcatcatt ttctgctccc tggtcctggg tgtcagcagc caaggatggt    660
taacattcct caaggcagct ggccaaggtg aggtccacag gataggggc aggaggctgc    720
ttctggctgc ccccaggatg cagctgagca gaggccacat ccccactggg caaaggtgct    780
agtgatgcca cagatggata gagaaggggc atggtttttc ataagcgtgg ttcctcatgc    840
ttttctggac agctttgaca ctcttctatg aggatcctcc agccgaggtc gcataaggtg    900
tgagctgcct cttttcagca ggaccatgag agagatgtgg agttgagggg tgcatgttcc    960
cataataccg gtgggctct actgcccct agtgggaaat ctgggacagt tcatgtctat   1020
gtctcctggg aagccaggaa gcaggtggat caaaagtgtg aggcgagtcc atgggaagc   1080
tgaacggagc caaccgtccc cataaaaaca accaagctta gctgagattt taatacgtac   1140
taggcactgt ttaaatgtac taatgaattg gtttccatca tttagtccta tgatgcaagc   1200
```

```
agcattatcc cttaacagag aagctaacac acacacacac acacacacac taacacacac    1260
acacacacac acacacacac aaacccccaag atacgtaaag aagttccaaa gcagagcagg    1320
attaacccag gcagtcttgc tctgcagaac ttgctcttaa tcaaggtact ctgctgcttt    1380
caaaacaaga gtttcggatt tgtgaacaca tagctcatcc tttatctaag aaatggcaaa    1440
taggatgtgt tgccttttgga aggtaagtct agctccactt atcccagtaa aacctacagt    1500
gaattacctt gatggtggtt ctactgggc ttatatatgg ccaggaaact gctagcaaga    1560
gaaatatacc ccgagggctg gcacagtgg ctcacacctg taatcccagc actttgggag    1620
gctgaggtgg gcagatcacc tgaggtcaag agttcgagac cagcctggcc aacatggcga    1680
aatcctgtct ctactaaaaa tacagaaatt agccgggtgt ggtggcatgc gcctataatc    1740
ccagcctctc gggaggctga gggagaagaa ttgcttgaac tcaggaggca gaggttgcag    1800
tgagctgtga tcacaccact gcactccagc ctaggagaca gagcaagact ccatctagag    1860
agacagagag agagagagag ggagaaatat accccactag ccataataaa gtggcaaaat    1920
tttgttttca gaatgcagta ttttaaattt caggtattat tatttttctg agtctctgaa    1980
aaatggtttt aaggatttgc ttttaatcct atttacatgt tcacacactc aactacaaat    2040
atctttcatt ccttaggtta atattttca aagggttgtt ctgggaccac ttgcgtgaga    2100
atcacctgga ttctgggatg ctttgtgaaa tgaaatgaag attcccgggt ccataccta    2160 cccctgccc ccaacagcca cagtctcttg ggacagagcc tagaaatctt gcctttgcta    2220
agcacctcgg tagattttta tgcacagcaa aggttgagaa ccactacctc ttgttttgct    2280
gctgaaagtg ataaaatgtg ccaggaattt tggaagtact tattaagcca atctgaacat    2340
caaggagcca tttaagtcag taactcagag gaataagtag agtaaaaatg tcataaactc    2400
tcaataaaag caatcaattt aacaccagga gtaataaatg cataaaatga agatgagtta    2460
tctaatagaa aaattatata aaccatgatt ataactctat atttgagttc ccccttttcc    2520
gtaatcagtt aattttctaa aaaatcttcg tcacttaatt ctagcttgat cagatccctt    2580
cagtccgtaa ctccctgctc ctcatcttag tttagcccctt ctttttttctt atgccacctt    2640 tcctaaggac cagagaagtg aaatgataat atattggcca cctacaatgt tctagacatc    2700
atacatgtat tttctctgct cttctgcata atcactgtga ggcaggcaat actcctccat    2760
ttcattgggg aggacattga ggttctgaac tagtgggtca gttgtccttt ttctgaattt    2820
gattacccag tagtataaag ctttcttagg taactcacct ttatcacttg ctgactgaat    2880
tctgacagat gtcagtttct aattatagcc tggacattca gatgtattca ggaccaagtt    2940
gtcctcactc tacctacagg catgaatttc tctcattgac taggttagga gcgccatatg    3000
tctgcagcct ccctcagaat cccctgtgtt ctcacaccag ggaactgagg gttccctggg    3060
tccttccagg tagaagttca ttgtacaatg aaacatccct taaggaccat ttcatctctt    3120
ctttaggtgc atcacacatg gttaaaacaa agtaataaca gaacttagaa tggaatcaaa    3180
cagaatgaaa cttacaccaa gtacaattct cattacatta acccagagaa gtgaaaagta    3240
gaagaatatt tatttcaagc caatataatt tccaagggct tgttgaagg ctgaaatctt    3300 cgggaggaaa gtagtgagaa gaaaactgtt cattcctcta tttctcccagt atataattgt    3360 tttgatcatt ttctttccctt tccagggact aaagacatgt ggaaagccta ctctgacatg    3420
aaagaagcca attacaaaaa attcagacaa atacttccat gcttggggga actatgatgc    3480
tgtacaaagg gggcttgggg ctgtctgggc tacagaagtg atcaggtaat gcacattcct    3540
```

-continued

```
gatgttgcca ggaatgagtg agcagagctt gactgccttg gacagtcagg agagaggtaa      3600
gctccttgca gagaagttag aggctgcagc ccctcctcct cttgccctct ctctgcctgt      3660
gtgcttagtg cgagggtctg agtggatggt agaagtgagt gattcctcac cctccctctc      3720
tgggtgctgt tcatccagcc tagggtgcc cagcctggct gagtggggca gtgcccaggc       3780 aggtcattg ttttcacccc tccttccttg gccttcctgg gcttctccca gagtcctccc       3840
ttggaaagca gagaatggga aggtgggctg ttgctcactg gcctggtgat taatctcctt      3900
gcttgcctgg actacagcga tgccagagag aacgtccaga gactcacagg agaccatgca      3960
gaggattcgc tggctggcca ggctaccaac aaatggggcc agagtggcaa agaccccaat      4020
cacttccgac tgctggcct gccagagaaa tactgagctt ccttttcaat ctgctctcag       4080
gagacctggc tgtgagcccc tgagggcagg acatttgtt gacctacagt tactgaattc       4140
tatatcccta gtacttgata tagaacacat aaaaatgctt aataaatgct tgtgaaatcc      4200
agtttgttat tggaatctgg aagcagaata tgacagtctt cctgggatca tgggcctgtt      4260
tagtaccata gggatgacca ataaac                                           4286

<210> SEQ ID NO 6
<211> LENGTH: 193
<212> TYPE: DNA
<213> ORGANISM: homo sapiens

<400> SEQUENCE: 6
gttttctgct ccttggtcct gggtgtcagc agccgaagct tcttttcgtt ccttggcgag       60
gcttttgatg gggctcggga catgtggaga gcctactctg acatgagaga agccaattac      120
atcggctcag acaaatactt ccatgctcgg gggaactatg atgctgccaa aggggacct      180 gggggtctgg gct                                                         193

<210> SEQ ID NO 7
<211> LENGTH: 64
<212> TYPE: PRT
<213> ORGANISM: homo sapiens

<400> SEQUENCE: 7

Val Phe Cys Ser Leu Val Leu Gly Val Ser Ser Arg Ser Phe Phe Ser
1               5                   10                  15

Phe Leu Gly Glu Ala Phe Asp Gly Ala Arg Asp Met Trp Arg Ala Tyr
            20                  25                  30

Ser Asp Met Arg Glu Ala Asn Tyr Ile Gly Ser Asp Lys Tyr Phe His
        35                  40                  45

Ala Arg Gly Asn Tyr Asp Ala Ala Lys Arg Gly Pro Gly Gly Leu Gly
    50                  55                  60

<210> SEQ ID NO 8
<211> LENGTH: 369
<212> TYPE: DNA
<213> ORGANISM: homo sapiens

<400> SEQUENCE: 8
atgaagcttc tcacgggcct ggttttctgc tccttggtcc tgagtgtcag cagccgaagc       60
ttcttttcgt tccttggcga ggcttttgat gggctcggg acatgtggag agcctactct      120
gacatgagag aagccaatta catcggctca gacaaatact tccatgctcg gggaactat      180 gatgctgcca aaggggacct ggggtgcc tgggccgcag aagtgatcag caatgccaga       240
gagaatatcc agagactcac aggccatggt gcggaggact cgctggccga tcaggctgcc      300
```

```
aataaatggg gcaggagtgg cagagacccc aatcacttcc gacctgctgg cctgcctgag    360
aaatactga                                                            369
```

<210> SEQ ID NO 9
<211> LENGTH: 122
<212> TYPE: PRT
<213> ORGANISM: homo sapiens

<400> SEQUENCE: 9

```
Met Lys Leu Leu Thr Gly Leu Val Phe Cys Ser Leu Val Leu Ser Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Ala Trp Ala Ala Glu Val Ile Ser Asn Ala Arg
65                  70                  75                  80

Glu Asn Ile Gln Arg Leu Thr Gly His Gly Ala Glu Asp Ser Leu Ala
                85                  90                  95

Asp Gln Ala Ala Asn Lys Trp Gly Arg Ser Gly Arg Asp Pro Asn His
            100                 105                 110

Phe Arg Pro Ala Gly Leu Pro Glu Lys Tyr
        115                 120
```

<210> SEQ ID NO 10
<211> LENGTH: 369
<212> TYPE: DNA
<213> ORGANISM: homo sapiens

<400> SEQUENCE: 10

```
atgaagcttc tcacgggcct ggtttttctgc tccttggtcc tgagtgtcag cagccgaagc    60
ttcttttcgt tccttggcga ggcttttgat ggggctcggg acatgtggag agcctactct   120
gacatgagag aagccaatta catcggctca gacaaatact ccatgctcg ggggaactat    180 gatgctgcca aaggggacc tgggggtgcc tgggccgcag aagtgatcag caatgccaga    240
gagaatatcc agagactcac aggccgtggt gcggaggact cgctggccga tcaggctgcc    300
aataaatggg gcaggagtgg cagagacccc aatcacttcc gacctgctgg cctgcctgag   360
aaatactga                                                            369
```

<210> SEQ ID NO 11
<211> LENGTH: 122
<212> TYPE: PRT
<213> ORGANISM: homo sapiens

<400> SEQUENCE: 11

```
Met Lys Leu Leu Thr Gly Leu Val Phe Cys Ser Leu Val Leu Ser Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60
```

```
Arg Gly Pro Gly Gly Ala Trp Ala Ala Glu Val Ile Ser Asn Ala Arg
 65                  70                  75                  80

Glu Asn Ile Gln Arg Leu Thr Gly Arg Gly Ala Glu Asp Ser Leu Ala
                 85                  90                  95

Asp Gln Ala Ala Asn Lys Trp Gly Arg Ser Gly Arg Asp Pro Asn His
            100                 105                 110

Phe Arg Pro Ala Gly Leu Pro Glu Lys Tyr
        115                 120

<210> SEQ ID NO 12
<211> LENGTH: 10001
<212> TYPE: DNA
<213> ORGANISM: homo sapiens

<400> SEQUENCE: 12
```

| | | | | | |
|---|---|---|---|---|---|
| gggtggatca | cgaggtcagg | agatcgagac | catcttggct | aacatggtga | accccgtct       60 |
| ctactaaaaa | tacaaaaaaa | ttagccgggc | gtcatggtgg | cgcctgtag | tcccagctac     120 |
| tcgggaggct | gaggcaggag | aatggtgtga | acccgggagg | cagaacttgc | agtgagccta     180 |
| gatcgcgcca | ctgcactcca | gcctggggga | caaaacgaga | ctctgtctca | aaaaaaaaaa     240 |
| aaaaaattcc | cacattagag | ttggggaaat | gggcagtcct | ggtggaagtt | agggaacaga     300 |
| tctgggacac | gttatagcca | gctggactac | aggaggccat | aagctcaatt | cttccttgac     360 |
| tctgaaacct | tccactggtc | ctaatgccta | gtaattccag | gcctttccca | gttgtgccag     420 |
| gcttggaggt | gaacacatct | atgtgccaag | aaggaaaggt | atgccaagca | ggggcttaag     480 |
| tcatccttat | cctcagtctg | tctatgagtg | gtatgtaccc | ctgttcccct | tgcaagatct     540 |
| gctgggctta | ggtctcctgg | ctgtgagttc | cccatacctg | gcataaatg | tagtgagcct     600 |
| gagctcccaa | ataaggttgg | gggctccaga | gaggtggaga | gccctgtgtc | tgggaagtgt     660 |
| gcccacccag | caggtctgac | caggaagata | cactgctagg | gttatggaaa | aagactatgt     720 |
| gtcaaggtct | cttgattctc | catctaggca | gagaatcatc | tttaattaat | gggaaactgg     780 |
| aaggcaaatt | acttggacct | gaaattactt | tttgtttatt | gaaccactgt | gttgtaaatc     840 |
| acatctctct | gaaggcaaga | gaaatcaggg | agttacaaaa | tgtttaggag | aactaaacag     900 |
| gactccctgt | tttgctaact | aatcagattg | agacaggctc | tctggtaaat | ctacaaattt     960 |
| gatgttgttc | aaccataagc | agtaaatttc | ctatgctgga | ttttcctgac | aatgaatgta    1020 |
| aaaggaaaag | gagtcttttt | gacaaaatat | tttattgttc | atctaaactg | aaaaacttct    1080 |
| ctattttca | aaattgctat | acgtgtttaa | agatgtagat | atttgaatag | cctaactggt    1140 |
| acagaaggtt | taatgatgat | tcctaagaca | tacctataaa | ttacttgaaa | ttgaaacgaa    1200 |
| atttaagaag | aattattgga | attttcccct | tctcaaatga | gttcttagtt | tcataaatac    1260 |
| tatacaagtc | cataagagat | ttggggtttt | gagatgtctt | tttttttttt | ttttttcag    1320 |
| acggagtttc | actgttgttg | cctaggctgg | agtgcaatgg | cgtgacctca | gctcactaca    1380 |
| acctccacct | cccaggttca | agcgattttc | ctgcctcagc | ctcccaagta | gctgggatta    1440 |
| cagggacctg | ccacaacgcc | aagctaatgt | tttgtatttt | tagtagagat | ggggttcacc    1500 |
| atgttggcca | ggcttgtctg | gaactcctga | cctcaggtga | tccacccgcc | tataatttat    1560 |
| tactccctt | tgcaaatgtt | tgaaaaggaa | taaagtgcaa | tatttttaaa | cagaatgcag    1620 |
| agttctgttg | tcctttggca | ataccagttt | cagactctga | gagtggctct | tgctgttgcc    1680 |
| gacagtgggc | tgatgaccaa | atcccaacat | gccccgctg | cgagtccttc | ataacctgat    1740 |
| tcagtcatca | cttagaggcc | agcaggcttc | agggaggcgt | gagcctcagc | caacaaccta    1800 |

```
tagggaaga gacgcagaac tcaatgcaga caggtttgga ttctggtgcc tagagaatgc   1860
aacttggaaa ctctgagcca ggagaaaagg gttctctctc catgagagag tgtgggcttt   1920
gtgagaagcg acacacagca aacacaatta agagtccacc cctcagcggg gcgcaggggc   1980
tcacgcctgt aatcccagca ctttgggagg ccgaggcggg tggatcacga ggtcaggaga   2040
tcaagaccat cctggctaac acagtgaaac cctgtctcta ctaaaaatac aaaaaaatta   2100
gccgggcgtg gtggcgggcg cctgtggtcc cagctactcg ggaggctgag gcaggagaat   2160
ggtgtgaacc cggaggtgg agcttgcagt gagccgagat cgcgccactg cactccagcc   2220
tgggcgacag agcgagactc catctcaaaa aaaaaagaa aaagaaaaag aaaagagtc    2280 cgcccctgaa ttaaatagtt ggtccttttg tgttcctggt gattcacttg ctaagtggaa   2340
gaaacaggag ggaatctttt ctcctgccct cctggtaatc catagcccat ggcctggctt   2400
tacttctgta aagtgcagg agaccttttg acagctgagc catttcttat tttatttatt    2460
ttaataagag atggtaggaa tgagcaatga tattagtacc tggggactgt tgttcttaag   2520
gagaaacaat cttagaatga ttagtgatac cccttgcttt ctcttttctt tcattatact   2580
ttttgtacac atattttcc catttattta ttggaatctt actgatttat tataagtata    2640
agctttatgt ctacacatgt ataatcattt ttccccaagt ataagtctct ttttcatgga   2700
ggcacagcct agacctggtt agccgccatc tcccctcatt gtatgcccaa tatctattgt   2760
agtatctgct gcatagaagg cactcgatgc gtgaatggat aatgactgat gatgaatcaa   2820
taaataaatg gacatgtcat tgtaaaaaat tctaaaaatc tagaataaca caagctgttg   2880
gcactaccta gaaacacaga tgtaaaactt cctaggttgt gtttcaccat gggaacatgt   2940
ctttgaacaa aaatgggatc atattctatt gcactctttc ccttaagaga tacttctcca   3000
ggtcattaag tgctcttcca caatatcagt atatggcaga ggcaaggtca taccaggtct   3060
gtctgaaacc agggcttggc tcttaacttg cagccatact gcctccaagt ctaggtggct   3120 gggtttagg atctgtaatg ggaactcagt gtcacaacct ctactgggaa ggtattctgg    3180
tgttgcataa caggactttc tgttagagat aaccatggca aaatgaata gagacaaagt     3240 tcaggtttct gctgccagga gctgagattg ctgtgaccaa tggcattctc ccaaaccaaa   3300
taatccaacc tggaattacc ataaaccact cctcatcttt tcaaggggtg tccaagttcc   3360
cagaaaagaa catttgttaa gggatggagg caaggaggtg gagaagaaag agcactggcc   3420
aaggtatcat gagtgtcctg ggttctggtc cttgaataag ccatttatct tctctgcagc   3480
ttctccatct gataggagtt tggaggcaga gttttttctt aatgagcaaa agacagtcgt   3540
gcctaggaga tgtggtgtac atgttagaaa gaagggactg gctgtgactc tataaaagat   3600
gaattcatac aaaaacaaat tacccttcc cagggagaaa gtttggatcc agtaattaga    3660
gatctcaaaa agtagaagac ctgccctgtg aggcctgtgg cctccaagtt tgaatgctgt   3720
gtgtcagctt taaaaactag tttcttgctg ataaatgttt catattaagc atgtgttgag   3780
agtactcctt gcctaccttc actagccact gtttccttcc cctcctccct tgtcccttca   3840
ttctctccag aactttctgc taacttccat tctcttcagg acttcagcat ggtttgggaga   3900 agatcagaaa ggcatcctca ctgttttat tttagtccac ttgacctttg gggagtagtt    3960
ccactggctc ataagtatca gccccccata gcacagcacc ccacactgag cccggaagca   4020
ataaagaatc ccaatctgct gtcactaacc agcacgctca actgccatgc cctttactct   4080
tctcatctcc ctgctttcac gtcacaccaa ctaatttctc tatgagtcag cctcaactct   4140
```

```
cccaacactc tgcccaccct tcttctacta ccttccagtg agctcctcga aagaagggtc    4200
tgcggtgagg atgccccttt atctctgcct atttccttcc cattacaaaa acttgaaacc    4260
tgcctttccc atgttgattt cactttattc tcatctttac ccatggggta tgcctcctgc    4320
aattcctcct agacaataga atgagaaaga ggggtcctcg tcctctttgc tttccatgac    4380
catttctcca ttcttcacct ctgtgatgtg tcctctttga agtccctgat aaattcatta    4440
ccaccttctc tccagtctta ctaatgttat ctgcacaagt gatttccaaa caggaagatt    4500
ttcaaacact gattcctgaa gatcacccccc aactcgctga actgagacca agacctccaa    4560
gattatggct taggaatctg catttttttt ttttttttga gacaagagtc tcgctctgtt    4620
gccaggctag agtgcaatgg tggaatcata gctcattgta acctcaaact cctgggctca    4680
agtgatcttc ctgcctcagc ctcccaagta gtgaggacaa caggagtgtg ccaccatgcc    4740
cagctaattg ttaattttt gtagaaatgg agtctcacta tgttgctcgg gctggtctca    4800
aactcctgac cttaacccat cctccgcctc cgccccaaa agtgttggga ttacaggtgt    4860
gagccaccgt gcccagccta gaaatacccca ctagaagctt ctgtgtagac aatctgctta    4920
gtgatgtttg gagacaaagt acctctttat tgtattcatt gacaaaactc tccagtcctc    4980
tcccatcttc atggaaaatt ttcacagttc atttacggcc ctctttccaa cacattcact    5040
gccaatactc ttattgacaa taactgtatt gttgaacctt ccagtatcct gcattcccgg    5100
atcaaggccc cctcaaagcc ctgatatgca aatatctggg aaaagaatgt tccagaggaa    5160
aggaacagct aatccgaggc ccctagggta agatgtgcct gggggtttgg agaccagtgt    5220
ggccagagca aaatgagcag gaggagagaa ttggatgatg aggtacgaga ggaaggagtt    5280
aggacagttt gagtaaagtt tgaaaaccat tataagggct ttgacttcaa ctatgagtgg    5340
aagtggaatc ctccggagag ttttgaatgg agagtgatag aagttgtctt gtgttgtaac    5400
agtctggctg ctatactgaa aagagactag ttggcggcaa aggggaaat gtggaagcca    5460 gttaagaagc catcataacc cagaaggtga tgcctaataa catctctctg ggagcagcgg    5520
agagatgata agggtttgcc ttctgaatat gttttttgac aattaatgta aacatttcaa    5580
gtaggctgag attttattgc atattaacaa tgtccatgtt cactcgcggc agccgccccc    5640
ttctgcgcgg tcatgccgag ccagcacctg ggcctggaac tgggccgcag ccccagctt    5700 cacccaccac ctccctacca tggacccctg caaagtgaac gagcttcggg cctttgtgaa    5760
aatgtgtaag caggatccga gcgttctgca caccgaggaa atgcgcttcc tgagagagtg    5820
ggtggagagc atgggaggta agtaccacc tgctactcag aaggctaaat cagaagaaaa    5880
taccaaggaa gaaaaacctg atagtaagaa ggtggaggaa gacttaaagg cagacgaacc    5940
atcaactgag gaaagtgatc tagaaattga taaagaaggt gtgattgaac cagacactga    6000
tgctcctcaa gaaatgggag atgaaaatgt ggagataacg gaggagatga tggatcaggc    6060
aaatgataaa aaagtggctg ctattgaagt cctaaatgat ggtgaactcc agaaagccat    6120
tgacttattc acagatgcca tcaagctgaa tcctcgcttg gccattttgt atgcaaagag    6180
ggccagtgtc ttcgtcaaat tacagaagcc aaatgctgcc atccaagact gtgacagagc    6240
cattgaaata aatcctgatt cagctcagcc ttacaagtgg cgggggaaag cacacagact    6300
tctaggccac tgggaagaag cagcccatga tcttgccttt gcctgtaaat tggattatga    6360
tgaagatgct agtgcaatgc tgaaagaagt tcaacctagg gcacagaaaa ttgcagaaca    6420
ttggagaaag tatgagcgaa acatgaagaa gcgagagatc aaagaaagaa tagaacgagt    6480
taagaaggct caagaagagc aggagagagc ccagagggag gaagaagcca gacgacagtc    6540
```

-continued

```
aggagctcac tatggcccctt ttccaggtgg cttttcctggt ggaatgcctg gtaattttcc    6600
cggaggaatg cctggaatgg gaggggacat gcctggaatg gccggaatgc ctggactcaa    6660
tgaaattctt agtgatccag aggctcttgc agccatgcag gatccagaag ttatggtggc    6720
cttccaggat gtggctcaga acccagcaaa tatgtcaaaa taccagagca acccaaaggt    6780
tatgaatctc atcagtaaat tgtcagccaa atttggaggt caagcataat gcccttctga    6840
taaataaagc cctgctgaag gaaaagcaac ctagatcacc ttatggatgt cgcaataata    6900
caaaccaacg tacctctgac cttctcatca agagagctgg ggtgctttga agataatccc    6960 taccccctctc ccccaaatgc agctgaagca ttttacagtg gtttgccatt agggtattca    7020
ttcagataat gttttcctac taggaattac aaactttaaa cacttttttaa atcttcaaat    7080 atttaaaaca aatttaaagg gtctgttaat tcttatatttt ttctttacta atcattgtgg    7140 attttttcctt aaattattgg gcagggaata tacttatttta tggaagatta ctgctctaat    7200
ttgagtgaaa taaaagttat tagtgcgagg caaacataaa aaaaaaaagt ccatgttcat    7260
ctctaaatga catcattgtt ccaaagcttt tccattcttc ttaaccttcc acctgtcaat    7320
ctataggaga tgacttctcc tacttcactc atgcattgac tccttcaatc aataaaagtg    7380
actaagaacc tgctacaggt gaggtgctgt gtttggtgtt aaagtgacaa cagttatctg    7440
tcaataagcc tgacaaggtt cctatccctg tgttttgtgc actctgggtc aaactcagaa    7500
atgcaaacag gtggagagcg atgagttcta tgactggtaa agaaaagggc ctgctggttt    7560
ccctcaggat ctctgtcctt catctcaaaa tgcatcttcc ttgttatcgt tcctctcctt    7620
cctgtctcag aggaagacct gctcctgcta cactctgggc aaccttgtcc ccgtggccct    7680
gtggcccctt ggttgttgaa gtctatgtta tgccctatct tttaccctca gtcactctct    7740
ctgttaacat tctccctgtg ccctgtaacc ctccctcatc tttaaataaa tcctcctcct    7800
ttgaccttcg catgtattca gtcatgcaac tcaacaagca tttattgcac agtgatattc    7860
aatttgccac ttgctaaaag tctgaacctt ggcagctgaa tgtgatcaga aaaaaagcac    7920
gactgctatg actagtctca ctttaaattc atggtcgttg accaagagct accatacaat    7980
ccactacctt tctcaagttc agtcacattc ttcctttcct agatgtctgc tttctacttc    8040
tcttctcttc tgaaacttcc cacaactcct cgttcattct cttctcagtt gacaactttg    8100 cttcctatttt cactgaaaaa tagaagcaat cagatatgaa cttctggctg gcatggtag    8160 ctcatgccta taatctcagc actttgggag gccaaggcag gaggactgca ggttaggaat    8220
ttgagaccag cctgggcaac atggtgaaac tcccactgta ctaaaaattt taaaaattac    8280
tcaaacatat tggcaaacaa ctgcagtccc agctacttgg gaggttgaga tgcaaggatc    8340
acttaaacct gggaggctga ggctgcagtg agccatgatt gcaccactgc actccagctc    8400
aggcaacaga gcaagacccct gtcttgagag gagaggagaa gagaggaggg gaggggaggg    8460
caggggaggg gaggggaggg gaagggagag gggaggggag aggggaggag agaggggagg    8520
ggaggggagg ggaggggagg ggaggagagg aggatcaggt gaggagtatg ccaaggagtg    8580
tttttaagac ttactgtttt ctcttttccca acaagattgt catttccttt aaaaagtagt    8640
tatcctgagg cctatattca tagcattctg aaagaaagaa aagaaaagag gaaagaaaga    8700
gagaggaagg aaggaaggag aaagagagag gaaggaagga gaaagagaga ggaaggaagg    8760
gaggaagaga agaagggagg aagaaaagaa ggaaggaagg agggagggag ggaagggagg    8820
gagggaaaga ggaagaaagg agggaaagaa ggaaggaaga gagagaggaa ggaaggagga    8880
```

```
agagagaaga aggaaggagg aagacagaga gggagtaagg aaggaaggaa ggagaaagag    8940
agaggaagga agaaatgaag gaaggaagga aagaaagaaa aaataaaaga gtgaaaacgg    9000
actggagaag aagaaaccac agttgctgct atatccacca gcctctctgc atgtcctggc    9060
ctcagccctg ctgggctctg gtactgacca cttccttcct tcctaatttc ctaattgact    9120
aggccagctg agcagggctt ttctgtgctg aggaggtaaa tctctggata tctagactga    9180
ggggtggaag gagccttcca gggcacacat gagacatggc aggggtaggc tgctagtttt    9240
attttgtttt cttttagaca cagggtcttg ctctgttaac caggctggag tgcagtggcg    9300
tgattatagc tcactgcagc cttgacctcc tgggtctccc acaatccttc cgcttcagcc    9360
tcttgagtag ctgggactgc aggtgcacac taccacaccc ggtccattta ttttatatt    9420 tcgtagagac aagatcttac agttttgcac agagtgatct taaactcttg accccaagtg    9480
atcctcctgc cttggcctcc aaaagcattg ggattatagg agtgagccac tgtgctggac    9540
ctagtctgtc agctttgaag ctttagatat gaactcagag ggacttcatt tcagaggcat    9600
ctgccatgtg gcccagcaga gcccatcctg aggaaatgac tggtagagtc aggagctggc    9660
ttcaaagctg ccctcacttc acccttcca gcagcccagg tgccgccatc acggggctcc    9720
cactctcaac tccgcagcct cagcccctc aatgctgagg agcagagctg gtctcctgcc    9780
ctgacagctg ccaggcacat cttgttccct caggttgcac aactgggata aatgacccgg    9840
gatgaagaaa ccactggcat ccaggaactt gtcttagacc gttttgtagg ggaaatgacc    9900
tgcagggact ttccccaggg accacatcca gcttttcttc gctcccaaga aaccagcagg    9960
gaaggctcag tataaatagc agccaccgct ccctggcagg c                      10001
```

<210> SEQ ID NO 13
<211> LENGTH: 10001
<212> TYPE: DNA
<213> ORGANISM: homo sapiens

<400> SEQUENCE: 13

```
gtctgccagg gagaggtggc tgctatttat agtgagcctt gctggtctct tgggagggaa      60
gaaaagctgg atgtggtccc tggggaaagt ccctgcaggt catttcccct acaaactggt     120
ctaagacaag ttcctggatg ccggtggttt cttcatcccg ggtcatttat cccagttgtg     180
taacctatgg gaacaagaga ggtttgctgt gccttggcaa tggacagggt gctagatcag     240
ctctgctcct cagcattggg ggaagtgcag ctgcagagat gccagtggga gccccgtgat     300
ggcggcacct gggctgctgg aaggtgtgga gtgagggcag ctcttcagcc agctcctgac     360
tataccggtc atttcctcag gatgggccct gctgggccac atggcagatg accctgactg     420
aaatccctgt gagttcatgt ctaaagcttt aagctttaaa acggacagcc tacccctgcc     480
acatctcatg tgtgccctgg aagcctcctt ccacccctct ggatgtcctg atatttctca     540
gcacagaaaa tctctgctcc gctggcttag ccaatttgga aatgcttttt ctaagttggc     600
tcctgagcca aggacaatgt agagagggggg actttctgct gccccagcct agtcctggag    660 cccccaccttg ggagaatgag agtgtggtgc gttaaatagg cagcccagct ggggacgtgc    720
ccagcatcca ggcagggaag ggtgggagag ctcttggtct gctgtattat cacggagggg    780 tgcaggggc atgcagatca ctctctcatg agaacatcaa caggggtcaga ttagctctgc    840 agaggcttat ggaggagcat ggtggccaga gatgggtcag taccagagcc caggggggct    900
gaggccagga catgcagaga ggctggtgga catagcagca actctggttt cttcttctcc    960
agtccatgtt catacccctga gggctaggca tttgtaataa caaacaaaca agcaatttag   1020
```

```
aaatgggcca ggcatggtgg catgtgccta tagtcccagc tacttgggag gccaaggcag    1080
gaggcctgct tgaacccaga aatttgaggc cagcctgggc aacacagcaa gattatctta    1140 aaaaatttt tttaatctct gagaaatggg tagggccagg aagtaaagga tggccaaata    1200
ctccataagc agcaaatgcg tggctccaat gtgaacaatg atattataga ctctgttctg    1260
agacctatgc attgacacct ccacctcccc cactacatct tgccaccta aaaccactga     1320 gagtggtacc tgctggaatg ggtccacaca cacagtcaca catattttag gcagggtagt    1380
tgacatcccc agggaaaaag agctcacaga gagaggctga atgtttccaa ctgggtagca    1440
gtaatagtac atcatgctgt acatggtaca gcacagatca ggtgaaaata atagcacatc    1500
gtgattaacc agggcttatt ccagggagtc aagaagagtt tcatatcaga aaatctatc     1560 tttgtaattc actataccag taatcaaaga aaaggattgt acatttattt tactagatgc    1620
agaaaatgaa tttcataatt gtcaacatct actgatgata aggaaaatgt ataacaaaat    1680
aaagagacca tttctgactt gagaaaggat aaataccaat atgttatagc aacagttctc    1740
aaactgtttt ccagggaacc ctaagaatcc ctccttaggg aggctttgat ctcaaaatta    1800
tttttagaat agtgctaaca cactattttc atgtttcagt ctcattttct catgagtaca    1860
cacaatatga caagttagtt gatatgagtg tggatttcca catggtaact gacttttcag    1920
aagctaccac ttgttgagtt tggtataata tagaatagcc acaattatct aaaaatacca    1980
ttaaaataca ctcccccatt tcaactatat atctgtgtga ggctgaattt tcttcatata    2040
ctccaaccta aataacatat taaaacaggt tggatgatga atcagatagg aaaatccagc    2100
tatgaaaaaa aaatcagaca tgaaaaattt tcaaagggt aaaaccatag tactcttctt     2160
actttttttc ttttggaaga tggttatttt tcataaaaat atattattta tgttaacata    2220
tagaagatgg ataattttt gaagaattga taaatgttta aattttttct ttctattatg     2280
gtaaatactg atgaatagag tccccataaa taaaagttct ttgggtatt caataatttt     2340 taatagtgta atgggatcct gagaccaaaa ggtttgagaa tcattgctct acagcaaaca    2400
ttatgtgtaa ttaagacact tcaggtgcat tctcaagaag accaataaag aggccacaat    2460
ggcaggcgtg gtggctcaca cttgtaatcc aagaacttag agaggacgag gcaggtggat    2520
cactggaggt caggaattct caaccagcct ggccaacatg gtgaaaccct gtctctacta    2580
aaagtacaaa aattagtcgg gtgtagtggc aggtacctgt aatcccaagt acttgggggg    2640
ttgaggcagg agaatcactt gaagccggga ggtggaggct gcagtgagcc gagatcgtgc    2700
cactgcactc cagcctgggc aacggagtga gacttcatca tggaaaaaaa aacaaagagg    2760
ccaggatgtc tggttgttac tgccactgtt tcacatatcc ctgaaggacc tgcccaatgc    2820
taaagaaaca caaggaaggt aagaggtgaa agagaagaaa tgaaactatc attgtttgaa    2880
gatgacacca tcttttacat agaaaacctg ttagaatcaa atggcaagct attagaacta    2940
ctaagagaat tcagtgaggc tgctgtattc atggcaaaat tttaacaatt gatagcattt    3000
ctctgcaaca ttccttaata gttataaaat acagcacaaa gtagtaccaa aaatattaac    3060
tatctaggaa ataacctctt acagagaaaa tttagtctgt taaaggataa acagtggcaa    3120
tgtacgtcat gtccacagag attatatttt agcttagcaa agataccaat tctcccaaat    3180
ttatttataa attaaatgca atgtgaatca aaatttccca ctggaatttt tatcaggaag    3240
gcaacaaatt ctttctttct ttctttcttt ctttctttat ttatttattt atttatttat    3300
ttatttattt ccttccttcc ttccttccctt ccttccttcc tttctttctt tctttcttc   3360
```

```
tttctttctt tctttctctc tctctttctc tctcccccc tctctctctc tctgtctctc      3420
tctctctctc tttctttctt tctttctttc tttcttttta agacaaagtc tggctctgtc      3480
acccaggctg cagtgcagtg atacaatctc agctcactga aacctcaacc tctccggcat      3540
caggtgaacc tcccacctca gcccccgag tagctgggac tacaggtgca caccactggg       3600
cctagataac tttttgtatt tattgtaaat aaacacaaaa aataaatatt ttgctcaggt      3660
tggtctggaa ctcctgggct caagcaatcc gcctgccttg gcctcccaaa gtgctagaat      3720
tacagttgtg agccaccaca cccagccaat aaattaattc tttatgatga ataagttatc     3780
tatgaaaatt aagtcagctg ggtgcggtgg ctcacgcctg taatcccagc actttgccgg      3840
gctgaagcag gtggatcacc tgaggttggg agttcaagac cagccggacc aacatagaga     3900
aaacccgtct ctactaaaaa tgcaaaatta gctgggtgtg gtggcatatg cctgtaatcc      3960
cagatactta ggaggctgag gcaggagaat tgcttgaacc cgggcggtgg aggttgcggt      4020
gagccaagat tgcaccattg cactccagcc tgggccacaa gagcgaaact ccatctcaaa      4080
aaaaaaaaaa gagaagttaa gtcaatgaaa agttaagtca attaaaaaag taagagctgt       4140
agtgtttaga tatatacaca cacacatata tatatattta tctttatata tgtatatata     4200
tcttttcctt ttttgagac cgagtctgtt tttgttgccc aggctggaat gcagtggcgc      4260
gatctctgct tactgcaacc tctgcctccc aggttcaagc gattctcgtg cctcagcctc     4320
ccgagtagct gggattacag gtgcctgccc ccatgcccgg ctaattttg cattttagt       4380 agagacgggg tttcaccatg ttggccaggc tggtctcaaa ctcctgacct caggtgatcc      4440
accggcctca gcctcccaaa gtgctgggat tacaggtgtg agccaccgcg cccagccata      4500
tattttgctt ttcatctgca gctcctggat cctaactcct tgttatattg ttgggcactt      4560
taggcctcag taaacagaat ctctgtctat gaccttctcc tgtccttctt ccacctgccc      4620
aaagcaggac tctaatttga ttgtgggtca aaagactctc attccagaaa gggccttgcc     4680 tcataccta gaggaaggaa tgctgcacag aaacgccaag tctgaacaga caagccttgc      4740
tgggtttata ccatatgctt tttgtccaat cacatttctt catggttgcc aatcatgcct      4800
atgtaatgaa gcctccataa gaacccagaa ggacagggtt cagagagttt ccacatagct     4860
gaacactatc tggagagtga acacttccta gagagtggca cacccagaga gatcatgaaa      4920
gctccacgcc cctttcccct tacctcgccc tccacatctc ttcatctgta tctttcataa      4980
tatcctttat aaataaacca gcaaatgtgt ttccctgagt tatgtgagtc actctagcaa     5040
attaatcgaa cccaaagagg gggtcatggg aaccccaact tgaagccagt cagtcagaag     5100
ttccagaggc ccagacttgc aactggggag aaagaggggg aggtcttggg gactgagccc     5160
ccaacctgtg ggatctgaca ctgtctccag gtaggtagtg ttggaactgc attggaggac     5220
actcctggtg tctgctgctt ggtgtgtggg gggaaaaacc cacacctttg gttacggagg    5280
tcttctgtgt tgacgatcat tgctgtttga gggcagaggg aatacacggt ttgagagagt   5340
ttttccctga catgagcgaa caggggacat gtactggtct ctgagatggg ggatcatggg     5400
atctgccaca agtgggggaga ccactgtgac ccctgccaca gtctttgggg cagagggtgt   5460 ctcggggca gaagaagcga gagttgtttg cagtagcagt tatgtccaaa gtgggcgcca     5520
ggaaagtagg gctgcccagc tttgaagagc ctccttactc ccagcctgaa tgaaaccatt     5580
tcctgtaaag cgctaagcat aaagtttgcc aatggtgatc cacggagaag tgagtgtacc    5640
ccaccccgcc atcccacagg gaatgtcgga gtgatgttga tctgcaccta ggaaggaat     5700 ggttcatgag atgtggtgga gatgctgagg gcccgtggac atcagatcct accctacctg    5760
```

-continued

```
tgccaggaca agccatgcgc atgtgcttca gaccaccagg caacaggagt gttgcatgag    5820
gtgtgaagca ggcacctggg aaagaggagt gtgaacagca gatgggacac actggggca     5880 gtcataggaa tgaaatgtcc caggatggat gcaggcaggt tatggaggac ttagtgagga    5940
ctgctctcct ggtgggaatt gtggagtggg agactggatg gagactggag gtgttttaag    6000
tagggaagcc aacttgcaag ggtgaccagg gaaactatgt cggccaaggg tgagacatgc    6060
actggcaaga ctctcagaca gcctggctta tctaagcaga atgcttgagc catgccaacg    6120
gtgcctcgca agttgtatta atcatgtcct ttcattttgt gttttggtg cttggcatct     6180 gggcccttgc tgaccctaag ggaccatttc tctcagagct agtcaagtcc tagacacagt    6240
aaatgactct cctgggagca tgccttccat gtgcagacca accaatcaag agtccacact    6300
cccacccacc tcctttatcg agctctcaca tcctggggca ccatccacct gccctaatca    6360
ctcaaggacc acgtcccaaa caactaggga cagcctccat gccctgcac ccattgaaat     6420 tattcatgct agccaatcct aaacctgtgt atgctgccac accattcctt cctgcagaaa    6480
cacagtaagg actcttccta cacctcccct acttcctctg ctccctgact tacccactta    6540
cttcctggtg cagtcccctg tggcatagtt cactctcttc ttttgggaac tgtgaggcta    6600
tcttctcaat ggcagtcatc tcctgagctg ttggccttgc catacctaac taataataaa    6660
atctatattc taaggtaaaa acaaaacaga tagggtctca ctctgttgcc caggctggag    6720
tacagtggtg tgatcatgac tcactgcagc ctcaaactcc tgggctcaag cagttctctc    6780
atctcaacct cccgagtagc tgggactaca ggcacacacc accatgcctg gctagttttc    6840 ttatttttt tgtagataca gggtcttgtt atgttgccaa ggctggtctt gaactcctgg      6900
gctcaagtga tcctcctgcc ttggcctccc aaactgctgc aattacaggc atgagccacc    6960
atgcccagat cagaaatctt actaaaaata tttcaaggag aagagaaagc caaagatgtt    7020
gaatatatat atatgtgtgt gtgtgtgtgt gtatatatat gtatatatgt gtatatatgt    7080
gtgtatatat atatgtatat atgtatatat atatgtatat atgtatatat atatgtatat    7140
tggggcaggc gtggtggctc atgcctgtgg tcctaactac ttgagagtct gaggtgggag    7200
gattgcttga gcctgggaga tcgaggctgc tgtgagctga gactacacca ctgcactcca    7260
gcttgggtga cagagtgaga ccctgtctcc aaaaaaacaa aaagaaaaag aaaaaaagat    7320 ggaaaagac atgaaaaac aacaacagaa atacccacac atcatcaatg ggagggaagc       7380
atcttgaggc agcaaagcgg gagtgctagt agagaggcag atagggcgtt ggacctgagg    7440
cattaaggaa agtcaggatt tggagcttac aagtctctca ttggagatgg gatggggttg    7500
gaatgaatgt ctgagcaaac acaaagcatt tccttcccta atgactcccc accagtctaa    7560
agaatcccac attaggtcga acacggtggc tcacgcctgt aatcccagca ctttgggagg    7620
ccaaggcggg tggatcacga ggtcaggaga tcgagaccat cttggctaac atggtgaaac    7680
cccgtctcta ctaaaaatac aaaaaatta gccgggcgtc atggtgggcg cctgtagtcc      7740
cagctactcg ggaggctgag gcaggagaat ggtgtgaacc cgggaggcag aacttgcagt    7800
gagcctagat cgcgccactg cactccagcc tggggggacaa acgagactc tgtctcaaaa     7860 aaaaaaaaa aaattcccac attagagttg gggaaatggg cagtcctggt ggaagttagg     7920
gaacagatct gggacacgtt atagccagct ggactacagg aggccataag ctcaattctt    7980
ccttgactct gaaaccttcc actggtccta atgcctagta attccaggcc tttcccagtt    8040
gtgccaggct tggaggtgaa cacatctatg tgccaagaag gaaaggtatg ccaagcaggg    8100
```

```
gcttaagtca tccttatcct cagtctgtct atgagtggta tgtaccccty ttccccttgc    8160
aagatctgct gggcttaggt ctcctggctg tgagttcccc atacctgggc ataaatgtag    8220
tgagcctgag ctcccaaata aggttggggg ctccagagag gtggagagcc ctgtgtctgg    8280
gaagtgtgcc cacccagcag gtctgaccag gaagatacac tgctagggtt atggaaaaag   8340
actatgtgtc aaggtctctt gattctccat ctaggcagag aatcatcttt aattaatggg   8400
aaactggaag gcaaattact tggacctgaa attactttt gtttattgaa ccactgtgtt    8460
gtaaatcaca tctctctgaa ggcaagagaa atcagggagt tacaaaatgt ttaggagaac   8520
taaacaggac tccctgtttt gctaactaat cagattgaga caggctctct ggtaaatcta   8580
caaatttgat gttgttcaac cataagcagt aaatttccta tgctggattt tcctgacaat   8640
gaatgtaaaa ggaaaaggag tcttttgac aaaatatttt attgttcatc taaactgaaa    8700
aacttctcta tttttcaaaa ttgctatacg tgtttaaaga tgtagatatt tgaatagcct   8760
aactggtaca gaaggtttaa tgatgattcc taagacatac ctataaatta cttgaaattg   8820
aaacgaaatt taagaagaat tattggaatt ttcccttct caaatgagtt cttagtttca    8880
taaatactat acaagtccat aagagatttg gggttttgag atgtctttt ttttttttt    8940
ttttcagacg gagtttcact gttgttgcct aggctggagt gcaatggcgt gacctcagct   9000
cactacaacc tccacctccc aggttcaagc gattttcctg cctcagcctc ccaagtagct   9060
gggattacag ggacctgcca caacgccaag ctaatgtttt gtatttttag tagagatggg   9120
gttcaccatg ttggccaggc ttgtctggaa ctcctgacct caggtgatcc acccgcctat   9180
aatttattac tccctttttgc aaatgtttga aaaggaataa agtgcaatat ttttaaacag  9240
aatgcagagt tctgttgtcc tttggcaata ccagtttcag actctgagag tggctcttgc   9300
tgttgccgac agtgggctga tgaccaaatc ccaacatgcc cccgctgcga gtccttcata   9360
acctgattca gtcatcactt agaggccagc aggcttcagg gaggcgtgag cctcagccaa   9420
caacctatag gggaagagac gcagaactca atgcagacag gtttggattc tggtgcctag   9480
agaatgcaac ttggaaactc tgagccagga gaaaagggtt ctctctccat gagagagtgt   9540
gggctttgtg agaagcgaca cacagcaaac acaattaaga gtccacccct cagcggggcg   9600
caggggctca cgcctgtaat cccagcactt tgggaggccg aggcgggtgg atcacgaggt   9660
caggagatca agaccatcct ggctaacaca gtgaaaccct gtctctacta aaaatacaaa   9720
aaaattagcc gggcgtggtg gcgggcgcct gtggtcccag ctactcggga ggctgaggca   9780
ggagaatggt gtgaacccgg gaggtggagc ttgcagtgag ccgagatcgc gccactgcac   9840
tccagcctgg gcgacagagc gagactccat ctcaaaaaaa aaagaaaaa gaaaagaaa     9900
aagagtccgc ccctgaatta aatagttggt cctttgtgt tcctggtgat tcacttgcta    9960
agtggaagaa acaggaggga atcttttctc ctgccctcct g                      10001
```